(12) United States Patent
Shoichet et al.

(10) Patent No.: US 7,928,129 B1
(45) Date of Patent: Apr. 19, 2011

(54) NANOMOLAR β-LACTAMASE INHIBITORS

(75) Inventors: Brian K. Shoichet, San Francisco, CA (US); Fabrio Prati, Reggio Emilia (IT)

(73) Assignees: Northwestern University, Evanston, IL (US); University of Modena, Reggio Emilia (IT)

( * ) Notice: Subject to any disclaimer, the term of this patent is extended or adjusted under 35 U.S.C. 154(b) by 0 days.

(21) Appl. No.: 11/901,810

(22) Filed: Sep. 18, 2007

Related U.S. Application Data

(62) Division of application No. 10/731,738, filed on Dec. 9, 2003, now Pat. No. 7,271,186.

(60) Provisional application No. 60/431,911, filed on Dec. 9, 2002.

(51) Int. Cl.
*G61K 31/69* (2006.01)
*G61K 31/445* (2006.01)
*C07F 5/02* (2006.01)

(52) U.S. Cl. ........ 514/370; 514/438; 546/190; 546/199; 564/123

(58) Field of Classification Search .................. 514/370, 514/438; 546/190, 199; 564/123
See application file for complete search history.

(56) References Cited

U.S. PATENT DOCUMENTS 4,963,655 A * 10/1990 Kinder et al. ................. 530/331

OTHER PUBLICATIONS

Kinder et al., "Acylamido boronic acids and difluoroborane analogs of amino acids," J. Med. Chem., vol. 28, pp. 1917-1925, 1985.*
Powers et al., Structures of Ceftazidime and its Transitional state analogues in complex with AmpC β-Lactamase, Biochemistry, vol. 40, pp. 9207-9214, 2001.*
Sperka, et al., Bioorganic & Medicinal Chemistry Letters, 15, 2005, 3086-3090, especially p. 3086, Col. 1, second paragraph.*
Powers, et al., "The complexed structure and antimicrobial activity of a non β-lactamase inhibitor of AmpC β-lactamase" Protein Science, 8, 2330-2337, published 1999.
Weston, et al., "Structure-based enhancement of boronic acid-based inhibitors of AmpC β-lactmase" J. Med. Chem., 41, 4577-4586, 1998.
Morandi, et al., "Nanomolar Inhibitors of AmpC β-lactamase" JACS, 125, 685-695, 2003.
Powers, et al. Structures of Cefazidime and Its Transition-State Analogue in Complex with AmpC β-Lactamase: Implications for Resistance Mutations and Inhibitor Design, Biochemistry, 40, 9207-9214, published on web Jul. 10, 2001.
Kinder, et al. "Acylamido boronic acids and difluoroborane analogs of amino acids," M. Med. Chem. vol. 28, pp. 1917-1925, 1985.

* cited by examiner

*Primary Examiner* — Susannah Chung
(74) *Attorney, Agent, or Firm* — Reinhart Boerner Van Deuren s.c.

(57) ABSTRACT

New carboxyphenyl-glycylboronic acid transition-state analog inhibitors, representative of a class of compounds effective against class C β-lactamase AmpC. The new compounds improve inhibition by over two-orders of magnitude compared to analogous glycylboronic acids, with Ki values as low as 1 nM.

7 Claims, 11 Drawing Sheets a.

b.

c.

d.

a.

b.

c.

R1 side chain    benzoic acid

R1 side chain    dihydrothiazine ring system a.

b.

a.

5b.

5c.

NANOMOLAR β-LACTAMASE INHIBITORS

This application is a divisional of and claims priority benefit from application Ser. No. 10/731,738 filed Dec. 9, 2003, issued as U.S. Pat. No. 7,271,186 on Sep. 18, 2007, and provisional patent application Ser. No. 60/431,911 filed Dec. 9, 2002, each of which is incorporated herein by reference in its entirety.

This invention was made with government support under Grant No. GM63815 awarded by the National Institutes of Health. The government has certain rights in the invention.

BACKGROUND OF THE INVENTION

Novel compounds are actively pursued as leads for drug discovery. Chemically, novel leads provide insight about the recognition determinants of the target receptor. Biologically, they can have specificities that substrate analogs lack and elude barriers or defenses to which substrate analogs fall victim.

The need for such new biological effects is keenly felt in the search for inhibitors of β-lactamases. These enzymes are the major resistance determinants of β-lactam antibiotics, including the penicillins and the cephalosporins, and threaten public health. To combat these enzymes, β-lactam inhibitors such as clavulanic acid, or "β-lactamase resistant" β-lactams such as ceftazidime, have been introduced (FIG. 1). The similarity of these β-lactams to the original substrates has allowed resistance to develop further. Broad-spectrum β-lactamases, such as the class C β-lactamase AmpC, have spread among bacteria. Point substitutions have resulted in mutants of once narrow-spectrum class A β-lactamases, leading to enzymes like TEM-30 and TEM-64 that are either less inhibited by, or can simply hydrolyze, the "β-lactamase resistant" compounds. Recently, new substrate analogs have been described that can inhibit these mutant and broad-spectrum β-lactamases with $IC_{50}$ values as low as 100 nM (FIG. 1). Given their similarity to substrates, resistance rapidly develops against these new agents as well.

A more ambitious strategy abandons substrate information altogether, focusing instead on the structure of the receptor as the sole template for design. Structure-based screening approaches have discovered inhibitors dissimilar to both substrates and substrate analogs. These novel inhibitors may evade traditional, pre-evolved resistance mechanisms. Conversely, however, these novel inhibitors of AmpC β-lactamase are relatively weak, with $K_i$ values in the 25 µM range.

Between the extremes of substrate analogs and structure-based discovery lie transition-state analogs (FIG. 2), such as boronic acids. These inhibitors replace the β-lactam recognition motif with a boronic acid, which makes a reversible, dative covalent bond with the active site serine residue forming a tetrahedral adduct (FIG. 2a).

Replacing the lactam group with a boronic acid permits evasion of many of the resistance mechanisms that now jeopardize β-lactams. By deploying side chains normally found in lactam substrates, it has been possible to improve the potency of these compounds, down to 5.9 nM for TEM-1. Glycylboronic acids (See FIG. 2b and Table 1, cpds. 1-4) were previously found to inhibit AmpC competitively, with $K_i$ values as low as 20 nM.

The glycylboronic acids resemble half of the β-lactam molecule, bearing the R1 side chain of substrates but lacking recognition elements corresponding to the thiazolidine or dihydrothiazine rings of penicillins or cephalosporins, respectively (FIG. 1a). The absence of a negatively charged group in a position corresponding to the C4' position of dihydrothiazine ring seems particularly noteworthy. All β-lactams bear a carboxylic or sulfonic acid at this position. In class A β-lactamases, this group is a key recognition element. In class C β-lactamases the role of this group is less understood. In fact, mutant and substrate analyses of the prior art suggest that such a charged group is not needed for recognition.

BRIEF DESCRIPTION OF THE DRAWINGS

FIGS. 5 and 6 were generated using MidasPlus.

FIG. 6. Overlay of the AmpC/16 and AmpC/2 complexes (PDB entry 1FSY for AmpC/2), each determined by x-ray crystallography.

SUMMARY OF THE INVENTION

In light of the foregoing, it is an object of the present invention to provide a wide range of compounds, compositions and/or methods for their use in the inhibition of β-lactamase enzymes, thereby overcoming various deficiencies and shortcomings of the prior art, including those discussed above. It will be understood by those skilled in the art that one or more aspects of this invention can meet certain objectives, while one or more other aspects can meet certain other objectives, each objective may not apply equally, in all its respects, to every aspect of this invention. As such, the following objects can be viewed in the alternative with respect to any one aspect of this invention.

It is an object of the present invention to provide one or more compounds or compositions that inhibit β-lactamase activity, absent a β-lactam ring structure, such compounds comprising glycylboronic acids and derivatives thereof, in particular, including phenylglycylboronic acids and m.carboxyphenylglycylboronic acids.

It can be another object of the present invention to provide one or more compounds, of the type consistent with the preceding objective, that inhibit β-lactamase enzymes with $K_i$ values as low as 1 nm and/or that can reverse β-lactam resistance.

It can also be an object of the present invention to identify structural or functional moieties for use in glycylboronic acid transition state analogs consistent with the preceding objectives, such compounds and compositions designed to target both recognition residues and/or resides outside β-lactamase recognition sites—utilizing thermodynamic cycle analysis in conjunction with a structure-based approach to maximize the interaction between β-lactamase inhibiting compounds/compositions and the β-lactamase enzyme.

It can be another object of the present invention to provide pharmaceutical compositions and/or compounds, including a glycylboronic acid such as phenylglycylboronic acid or m.carboxyphenylglycylboronic acid, and/or a pharmaceutically-acceptable salt thereof for the treatment of β-lactamase bacterial infections, such compositions and/or compounds including or provided in conjunction with a β-lactam antibiotic.

Other objects, features, benefits and advantages of the present invention will be apparent from this summary and its descriptions of various preferred embodiments, and will be readily apparent to those skilled in the art having knowledge of enzyme activity and the inhibition thereof. Such objects, features, benefits and advantages will be apparent from the above as taken into conjunction with the accompanying examples, data, figures and all reasonable inferences to be drawn therefrom.

Figure 1:
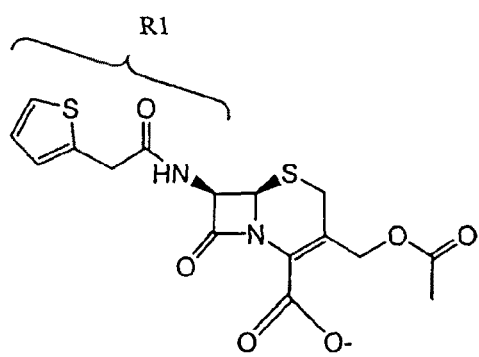
FIG. 1. Chemical structures of several β-lactam ligands; the R1 side chains are marked. (A) The substrate cephalothin, (B) The "β-lactamase resistant" ceftazidime, (C) The inhibitor ATMO-carbacephem, and (D) The inhibitor clavulanic acid.
Figure 1:
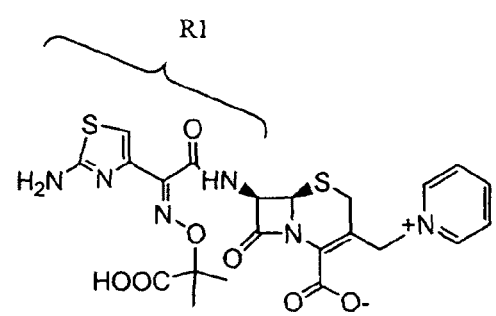
Figure 1:
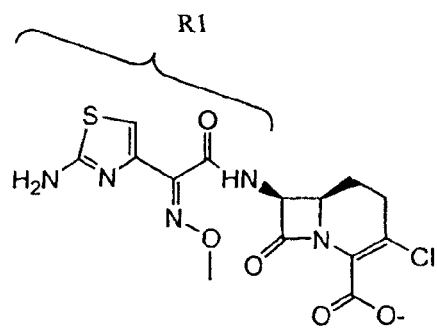
Figure 1:
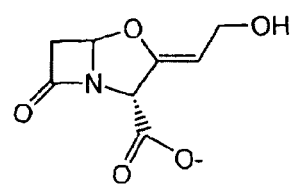
Figure 2:
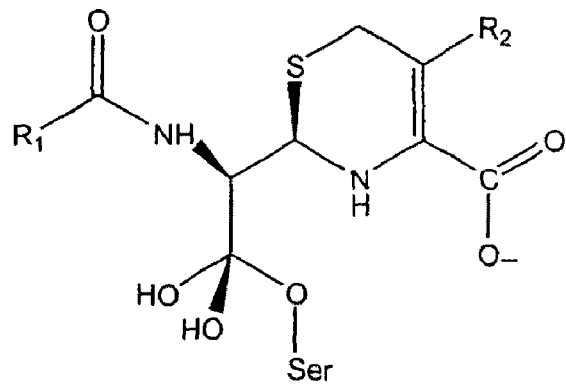
FIG. 2. Comparison between the deacylation high energy intermediate of a cephalosporin in a serine β-lactamase (A), a transition-state analog glycylboronic acid (B), and a transition-state analog m.carboxyphenylglycylboronic acid (C).
Figure 2:
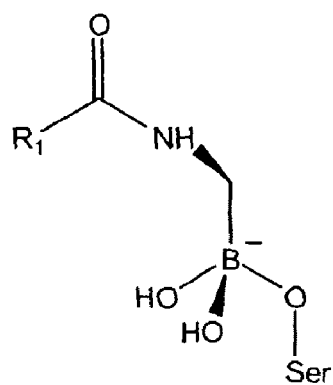
Figure 2:
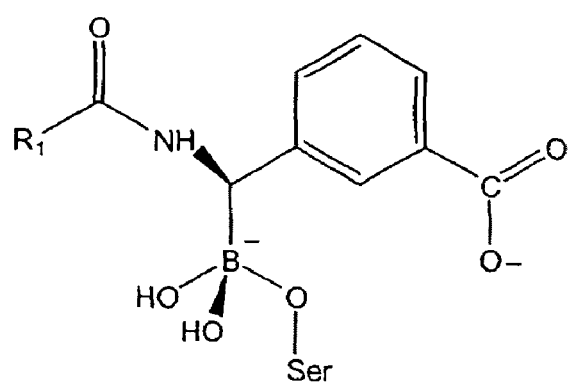
Figure 3A:
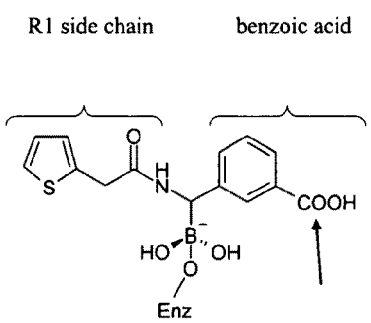
FIG. 3. Comparison of the covalent adduct of (A) compound 16, with (B) the high energy intermediate of the substrate cephalothin. Arrows indicate the carboxylate of interest.
Figure 3B:
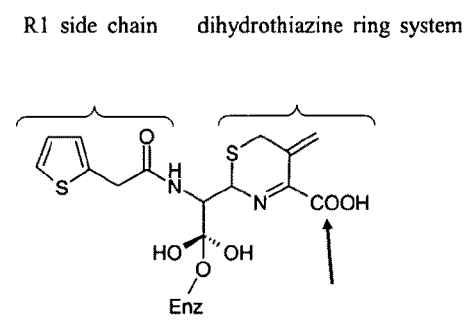

The present invention provides, in part, a structure-based approach to the design and testing of certain novel compounds including, but not limited to, phenyl and m.carboxyphenylglycylboronic acids (FIGS. 2c, 3a). The m.carboxylate group of such embodiments is meant to correspond to the C4' carboxylate of cephalosporins in their tetrahedral high-energy intermediate form, mimicking both the distance to the tetrahedral center and the absolute stereochemistry of the chiral carbon (FIGS. 2a, 3b). These and other structurally-related compounds improve inhibition by over two-orders of magnitude compared to prior art glycylboronic acids (e.g., FIG. 2b) that lack such structure. Since these inhibitors bind reversibly to the enzyme, the different $K_i$ values allow for a thermodynamic analysis of affinity. By making small or incremental substitutions or functional group additions to the inhibitors, the contribution of the phenyl, carboxylic acid, and other functional moieties to binding may be understood (Tables 1 and 6). The structures of AmpC in complex with two of these inhibitors, determined by x-ray crystallography, allow for investigation of the structural bases for binding. The selectivity of these inhibitors for AmpC versus characteristic serine proteases, which boronic acids are known to inhibit, is considered, as is their efficacy against pathogenic bacteria expressing class C β-lactamases.

For the purposes of the present compounds, compositions and/or methods, the following expression(s) and words, unless otherwise indicated, will be understood as having the meanings ascribed thereto by those skilled in the art or as otherwise indicated with respect thereto:

"Alkyl" refers to both straight and branched chain and cyclic saturated hydrocarbons, for example, methyl, ethyl, propyl, isopropyl, and the like. The alkyl moiety can be substituted by one or more groups including, but not limited to, hydroxy, halogen, alkoxy, amino, amido, nitro, nitrile, azo, aryl, acyl, carboxy, sulfoxy, sulfonyl, formyl, alkoxycarbonyl, aminocarbonyl, amidocarbonyl, arylcarboxamido, arylamino, arylcarbonyl, arylalkoxy, amidocarbonyl, carboxycarbonyl and/or combinations thereof.

"Alkenyl" refers to unsubstituted hydrocarbon chain radical having in certain embodiments from about 2 to about 8 carbon atoms. Representative alkenyls include, but are not limited to, vinyl, allyl, and isopropenyl. The alkenyl moiety can be substituted by one or more groups including, but not limited to, hydroxy, halogen, alkoxy, amino, amido, nitro, nitrile, azo, aryl, acyl, carboxy, sulfoxy, sulfonyl, formyl, alkoxycarbonyl, aminocarbonyl, amidocarbonyl, arylcarboxamido, arylamino, arylcarbonyl, arylalkoxy, amidocarbonyl, carboxycarbonyl and/or combinations thereof.

"Cycloalkenyl" means a structure containing one or more rings, each ring containing about 4 to about 10 carbon atoms and containing at least one double bond. Without limitation, one or more of the rings may be aromatic, thereby including an aryl (unsubstituted or substituted) moiety. In addition, one or more rings may be substituted by one or more functional groups. Representative cycloalkenyls include, but are not limited to, cyclohexdienyl, phenyl, biphenyl, napthyl, and benzyl.

"Heterocyclyl" or "Heterocyclic ring" refers to an unsaturated or saturated, substituted or unsubstituted, mono or multicyclic about 4- through about 10-membered heterocyclic ring containing one or more heteroatoms including but not limited to oxygen, nitrogen or sulfur. Representative heterocyclyl moieties include, but are not limited to, pyridinyl, pyrazinyl, thiophenyl, thiophenyl-2-yl, thiophenyl-3-yl, pyrrolyl, furanyl, thiazolyl, imidazolyl, indazolyl, benzothiophenyl, isoindolyl and oxazolyl.

As detailed below, with reference to schemes 1 and 2 and examples 1-10, below, the synthesis of (R)-[1-acylamino-1-(3-carboxyphenyl)]methylboronic acids 15-17 employed the general strategy developed by Matteson, et al (Scheme 1). Matteson, D. S., Ray, R., Rocks, R. R. and Tsai, D. J. S. *Organometallics* 1983, 2, 1536-1543. Matteson, D. S. *Acc. Chem. Res.* 1988, 21, 294-300. (+)-pinanediol was chosen as a chiral auxiliary to guide the stereochemical course of the Matteson homologation. Matteson, D. S. *Chem. Rev.* 1989, 89, 1535-1551. Matteson, D. S. *J. Organomet. Chem.* 1999, 581, 51-65. Protection of the carboxy moiety of 3-bromobenzoic acid 5 as the oxazolidine derivative 6, followed by boronation of the corresponding lithium derivative at −78° C. with $B(OCH_3)_3$ and trans-esterification with (+)-pinanediol, afforded the desired compound 7 (overall yield of 70% from compound 5). Compound 7 was converted in a "one pot" reaction to compounds 10-12 (16-25% overall yield) to avoid the epimerization of the intermediate α-chloro derivative 8. Occasionally compounds 8 and 9 were isolated and characterized. $^1$H NMR analysis of compounds 10-12, particularly the diagnostic signals of the amide NH peaks and the $H_{endo}$ hydrogen of the pinanyl moiety, showed greater than 98% diastereoselectivity of the "one pot" reaction. Attempts to synthesize 13 and 14 were not successful under the conditions employed, probably due to steric hindrance, as discussed above. Following the same protocol, compound 20 (Scheme 2) was obtained in 56% overall yield, starting from the (+)-pinanediol phenylboronate 19. The conversion of the pinanediol esters to the free boronic acids 15-17 and 21 was achieved through hydrolysis in degassed HCl under reflux for 1 hour. This treatment also led to the deprotection of the carboxy moiety. Compound 17 was obtained by extraction with EtOAc, and compounds 15, 16, and 21 were recovered from the aqueous phase. All compounds were fully characterized by $^1$H and $^{13}$C NMR, IR, mass spectra, and elemental analysis except for compounds 15-17 and 21, for which mass spectra were unobtainable. Nevertheless, the x-ray structures, combined with the NMR and IR analyses, unambiguously identified these compounds.

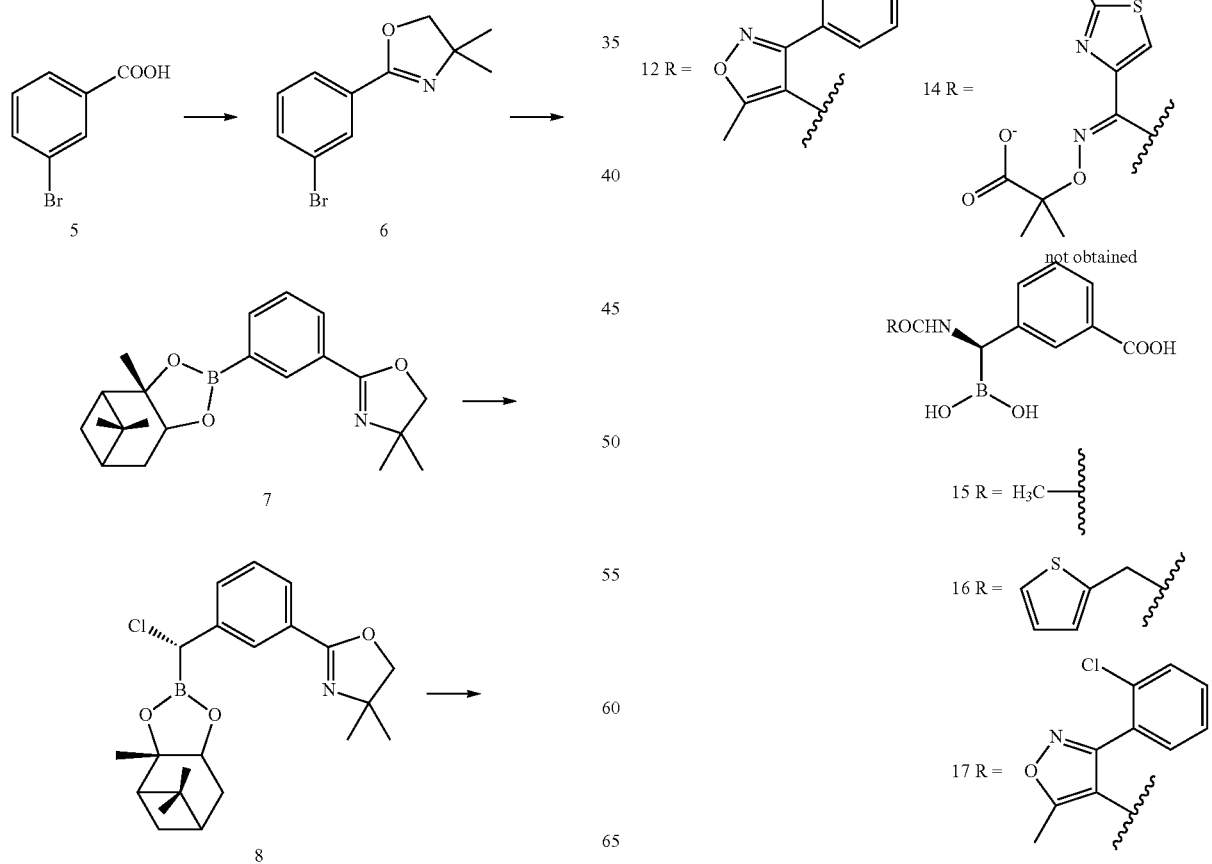

Scheme 1.

Scheme 2.

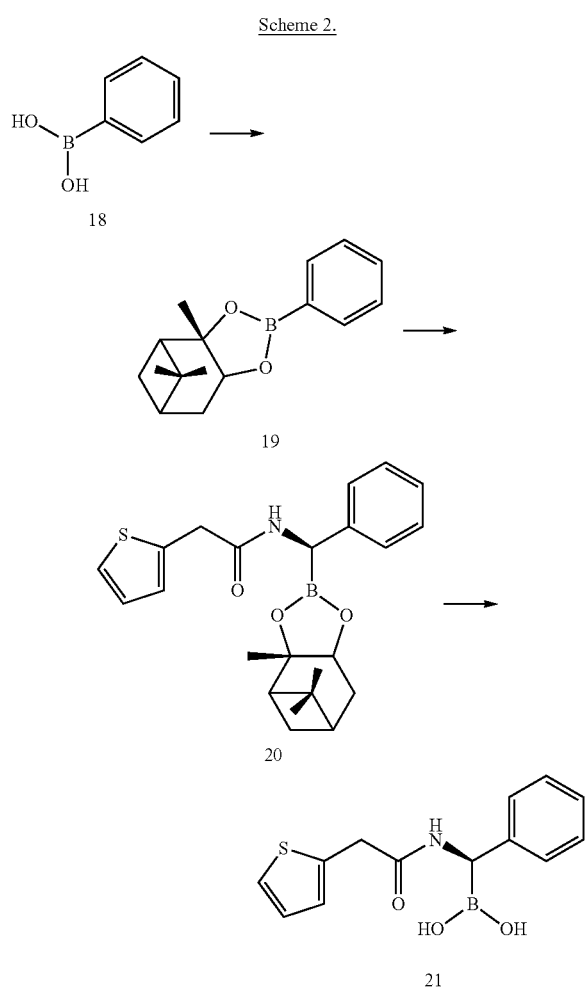

Notwithstanding the embodiments illustrated in Schemes 1-2 (and 3, below), various aspects of this invention may be more generally considered in conjunction with compositional compounds of the following structural formula.

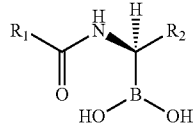

wherein, without limitation, $R_1$ can be a substituent corresponding or structurally similar to that of a recognized side chain of a β-lactam antibiotic, the general structures of which are known (see, e.g., *The Merck Index* (10th edition, Merck & Company, Inc., Rahway, N.J., 1983) and *Physicians' Desk Reference* (53rd edition, Medical Economics Company, Inc., Montvale, N.J., 1999)), as are the $R_1$ side chains thereof.

Notwithstanding above, the $R_1$ substituent can include hydrogen, alkyl, alkenyl, cycloalkenyl, and heterocyclyl moieties. The $R_1$ substituant can further comprise at least one moiety including, but not limited to, hydroxy, halogen, alkoxy, amino, amido, nitro, nitrile, azo, acyl, carboxy, sulfoxy, sulfonyl, formyl, alkenyl, branched or unbranched alkyl, cycloalkyl, aminoalkyl, alkoxylalkyl, carboxylalkyl, arylalkyl, haloalkyl, azoalkyl, amidoalkyl, alkylcarbonyl, alkoxycarbonylalkyl, alkoxycarbonyl, aminocarbonyl, amidocarbonyl, arylcarboxamido, arylamino, arylcarbonyl, arylalkoxy, amidocarbonyl, carboxycarbonyl, cycloalkenyl, heterocyclyl and combinations thereof. In specific embodiments, $R_1$ can comprise a thiophene-2-yl or a thiophene-3-yl substituted with an alkyl moiety.

As discussed more fully elsewhere herein, $R_2$ is a substituent which can be chosen on a structural basis, from a functional perspective, corresponding to the C3(4)' carboxylate of a β-lactam antibiotic, whereby such a substituent contributes to and/or enhances affinity for β-lactamase recognition. Such a substituent includes, but is not limited to, heterocyclyl, cyclo alkene, alkenyl and alkyl moieties. Consistent with the broader aspects of the present invention, the $R_2$ can be unsubstituted, or alternatively can be substituted with at least one substituent selected from hydroxy, halogen, alkoxy, amino, amido, nitro, nitrile, azo, acyl, carboxy, sulfoxy, sulfonyl, formyl, alkenyl, branched or unbranched alkyl, cycloalkyl, aminoalkyl, alkoxylalkyl, carboxylalkyl, arylalkyl, haloalkyl, azoalkyl, amidoalkyl, alkylcarbonyl, alkoxycarbonylalkyl, alkoxycarbonyl, aminocarbonyl, amidocarbonyl, arylcarboxamido, arylamino, arylcarbonyl, arylalkoxy, amidocarbonyl, carboxycarbonyl, cycloalkenyl, heterocyclyl and combinations thereof.

In preferred embodiments, the β-lactamase inhibiting compound is a phenylglycylboronic acid wherein $R_2$ is a phenyl substituted with a 3-carboxyate group.

In yet other embodiments of the present invention, $R_2$ can include a phenyl group substituted with a formyl, heterocyclyl or sulfonyl moiety, a functional group selected to exhibit a negative charge, and/or a C3(4)' anionic functional group of a β-lactam antibiotic, thereby enhancing the affinity for β-lactamase recognition.

Numerous other compounds, as can be used in conjunction with the present invention, can comprise structural or compositional (e.g., salts or ionic analogs) variations of $R_1$ and $R_2$, or a substituent thereof, providing the inhibitors of the present invention with significant binding, complexing and/or interactive capabilities with one or more β-lactamase substrates including those functional groups providing covalent or ion-dipole interaction with conserved (e.g. Asn343, Asn346) and unconserved (e.g. Asn289) residues of β-lactamase enzymes. Likewise, the compounds of this invention, irrespective of $R_1$ or $R_2$ identity, can further comprise functional group derivatives thereof (e.g., pinanediol and oxazoyl derivatives of boric acids 15-17 and 21).

By way of illustration, compounds 21, 16, 15 and 17 are shown, respectively, below, schematically designating several $R_1$ and $R_2$ side chains, each of which comprising a corresponding $R_1$ or $R_2$ substituent.

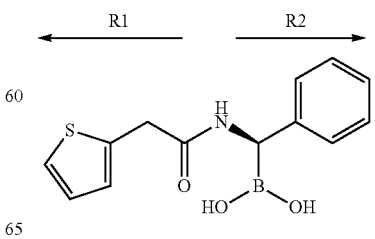

-continued

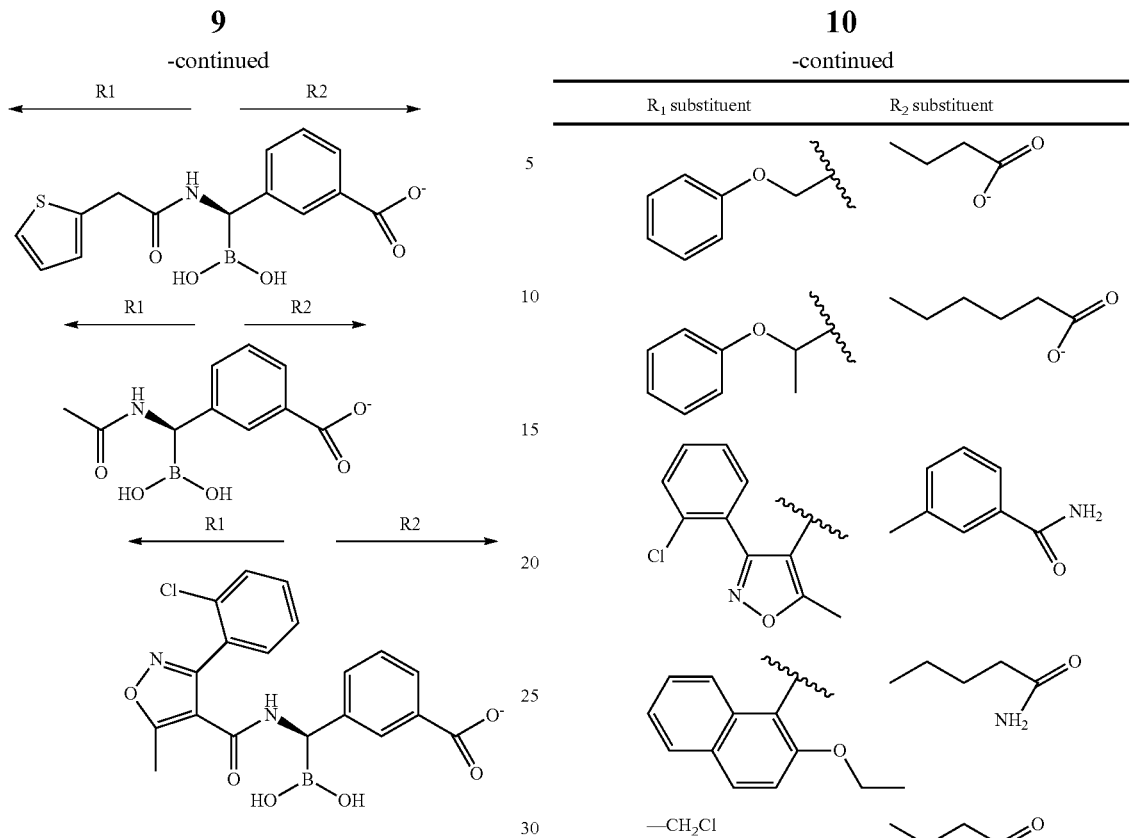

Without limitation, the present invention can further include compounds/compositions wherein $R_1$ and $R_2$ substituents can be selected independently from the structures provided below. In certain embodiments, as would be understood by those skilled in the art made aware of this invention, compounds having bulky $R_1$ side chains can be utilized with relatively small $R_2$ substituents. Conversely, relatively small $R_1$ substituents might be utilized, in certain embodiments, with bulky $R_2$ substituents. Likewise, while such compounds/compositions and associated methodologies are discussed herein in the context of inhibiting class C β-lactamases, it will also be understood by those skilled in the art that such compounds/compositions can be utilized to effect class A β-lactamase inhibition. Such compounds are prepared, from available reagents and starting materials, using the synthetic techniques and methodologies described herein or straightforward modifications thereof, as would be known to those skilled in the art made aware of this invention.

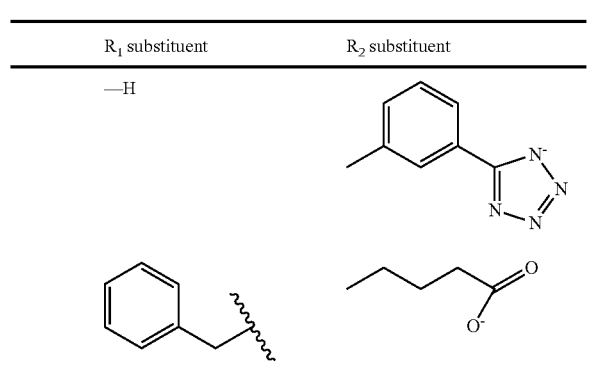

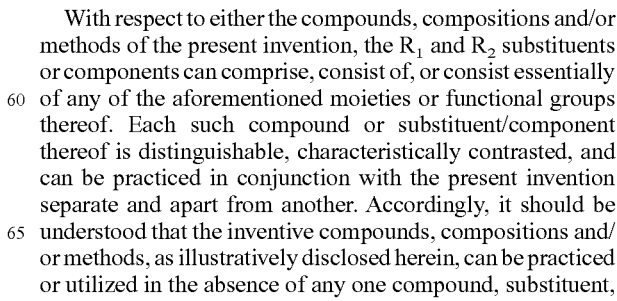

With respect to either the compounds, compositions and/or methods of the present invention, the $R_1$ and $R_2$ substituents or components can comprise, consist of, or consist essentially of any of the aforementioned moieties or functional groups thereof. Each such compound or substituent/component thereof is distinguishable, characteristically contrasted, and can be practiced in conjunction with the present invention separate and apart from another. Accordingly, it should be understood that the inventive compounds, compositions and/or methods, as illustratively disclosed herein, can be practiced or utilized in the absence of any one compound, substituent, component, moiety or functional group which may or may not be disclosed, referenced or inferred herein, the absence of which may or may not be specifically disclosed, referenced or inferred herein.

Enzymology and binding affinities. All boronic acids inhibitors of AmpC β-lactamase previously studied have been reversible, fast-on fast-off, competitive inhibitors. The phenylglycylboronic acids, especially the 1 nM inhibitor compound 16, showed time-dependent inhibition of AmpC Notwithstanding this, they were all reversible inhibitors, displaying classic time-dependent recovery from inhibition during a reaction initiated with substrate (i.e., reaction rates increased after an initial lag-phase, and then reached a steady-state plateau). The time-dependence in the inhibition thus reflects a slow off-rate. Consistent with reversibility, the inhibitors could be competed off by increasing substrate concentration. Perhaps the simplest model to explain the time-dependent effect with these inhibitors is a convolution of their high affinities—a nanomolar $K_d$ value alone would lead to an off-rate on the second time-scale—and the dative-covalent nature of the serine-boron bond. There was no significant conformational change in the enzyme site in the complexed structures, suggesting that enzyme reorganization did not present a significant barrier to inhibitor leaving the site. The incubation effect in the K, values reported for these inhibitors have been accounted for, as described below.

To investigate the effect on inhibition of adding an m.carboxyphenyl group, the potency of relatively simple derivatives bearing an acetyl R1 side chain (compound 15) and an R1 side chain resembling that of cephalothin (compound 16) was first measured. These compounds were 150-fold and 300-fold more potent than the lead compounds lacking the m.carboxyphenyl side chain, compounds 1 and 4, respectively (Table 1). In these compounds, the addition of the m.carboxyphenyl side chain improves binding energy by about 3 kcal/mol. Reference is made to example 11, below.

TABLE 1

$K_i$ values of the glycylboronic acids against AmpC

It was determined that if better leads than 1 and 4, which had inhibited AmpC with

| Compound | β-lactam analog | R$_1$ | R$_2$ | $K_i$ (μM) | ΔΔG$^b$ from 1 (kcal/mol) |
|---|---|---|---|---|---|
| 1 | — | —CH$_3$ | H | 18.5$^a$ | 0.00 |
| 15 | — | —CH$_3$ | (m-carboxyphenyl) | 0.13 | 2.95 |
| 2 | Cloxacillin | | H | 0.15$^a$ | 2.85 |
| 17 | Cloxacillin | (chlorophenyl-methylisoxazole) | (m-carboxyphenyl) | 5.7 | 0.70 |
| 3 | Ceftazidime | | H | 0.020 | 4.04 |
| 14 | Ceftazidime | (aminothiazole oxime) | (m-carboxyphenyl) | N.O.$^c$ | — |

TABLE 1-continued

K$_i$ values of the glycylboronic acids against AmpC

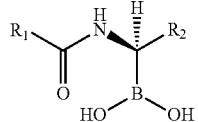

It was determined that if better leads than 1 and 4, which had inhibited AmpC with

| Compound | β-lactam analog | R$_1$ | R$_2$ | K$_i$ (µM) | ΔΔG$^b$ from 1 (kcal/mol) |
|---|---|---|---|---|---|
| 4 | Cephalothin | thiophene-CH$_2$- | H | 0.32$^a$ | 2.40 |
| 16 | Cephalothin | thiophene-CH$_2$- | phenyl-CH$_2$- | 0.001 | 5.82 |
| 21 | Cephalothin | | phenyl-CH$_2$- | 0.035 | 3.71 |

$^a$ These K$_i$ values were determined in 50 mM KPi pH 7.0. The values in Tris are typically two fold lower.
$^b$Differential free energy of binding relative to compound 1, calculated at 298 K.
ΔΔG = -RTlnK$_{i,N}$/K$_{i,1}$, where N represents the compound to which compound 1 is being compared. PositiveValues are calculated using values indicate improved affinity.
$^c$Not obtained.

K$_i$ values of 18.5 and 0.320 µM, respectively, were utilized, still better inhibitors could be achieved. Therefore, the m.carboxyphenylglycylboronic acid analogs of compounds 2 and 3, which had inhibited AmpC with K$_i$ values of 0.150 and 0.020 µM, respectively, were used (Table 1). Surprisingly, compound 17, bearing the R1 side chain of cloxacillin, was 40-fold less potent (higher K$_i$) than the original analog lacking the m.carboxyphenyl group (compound 2). For this compound, the addition of the m.carboxyphenyl group made the binding energy about 2 kcal/mol worse (Table 1). As indicated in Table 1, the analog bearing the ceftazidime side chain (14) was unable to be synthesized.

X-ray crystallographic structure determination. To investigate the structural bases for this dramatic reversal of relative affinities, and to understand detailed recognition, the crystal structure of AmpC in complex with 16 to 1.83 Å resolution was determined (Table 2). Excluding proline and glycine residues, 92.2% of the amino acids were in the most favored regions of the Ramachandran plot (7.8% in the additionally allowed regions). Reference is made to example 13, below.

TABLE 2

X-ray data collection and refinement statistics.

| Cell constants (Å; °) | a = 117.96 | a = 118.20 6 |
| | b = 77.49 | b = 76.70 |
| | c = 96.91 | c = 97.6 |
| Space group | C2 | C2 |
| Resolution (Å) | 1.83 | 1.72 |
| Unique reflections | 66946 | 82138 |
| Total observations | 257829 | 350811 |
| R$_{merge}$ (%) | 6.0 (42.5)$^a$ | 4.0 (12.0)$^a$ |
| Completeness (%) | 96.5 (91.0)$^a$ | 99.2 (96.0)$^a$ |
| <I>/<σ$_I$> | 19.5 (2.7)$^a$ | 30.0 (11.2)$^a$ |
| Resolution range for | 20.0-1.83 | 20.0-1.72 |

TABLE 2-continued

X-ray data collection and refinement statistics.

| refinement (Å) | (1.87-1.83)$^a$ | (1.76-1.72)$^a$ |
|---|---|---|
| Number of protein residues | 716 | 716 |
| Number of water molecules | 468 | 587 |
| RMSD bond lengths (Å) | 0.010 | 0.014 |
| RMSD bond angles (°) | 1.57 | 1.76 |
| R$_{cryst}$ (%) | 18.7 | 16.7 |
| R$_{free}$ (%) | 21.4 | 18.9 |
| Average B-factor, protein atoms (Å$^2$) | 34.8$^b$ | 22.7$^b$ |
| Average B-factor, inhibitor atoms (Å$^2$) | 44.5$^b$ | 36.1$^b$ |
| Average B-factor, water molecules (Å$^2$) | 39.1 | 34.1 |
| | AmpC/16 complex | AmpC/21 complex |

$^a$Values in parentheses are for the highest resolution shell.
$^b$Values cited were calculated for both molecules in the asymmetric unit.

Figure 4:
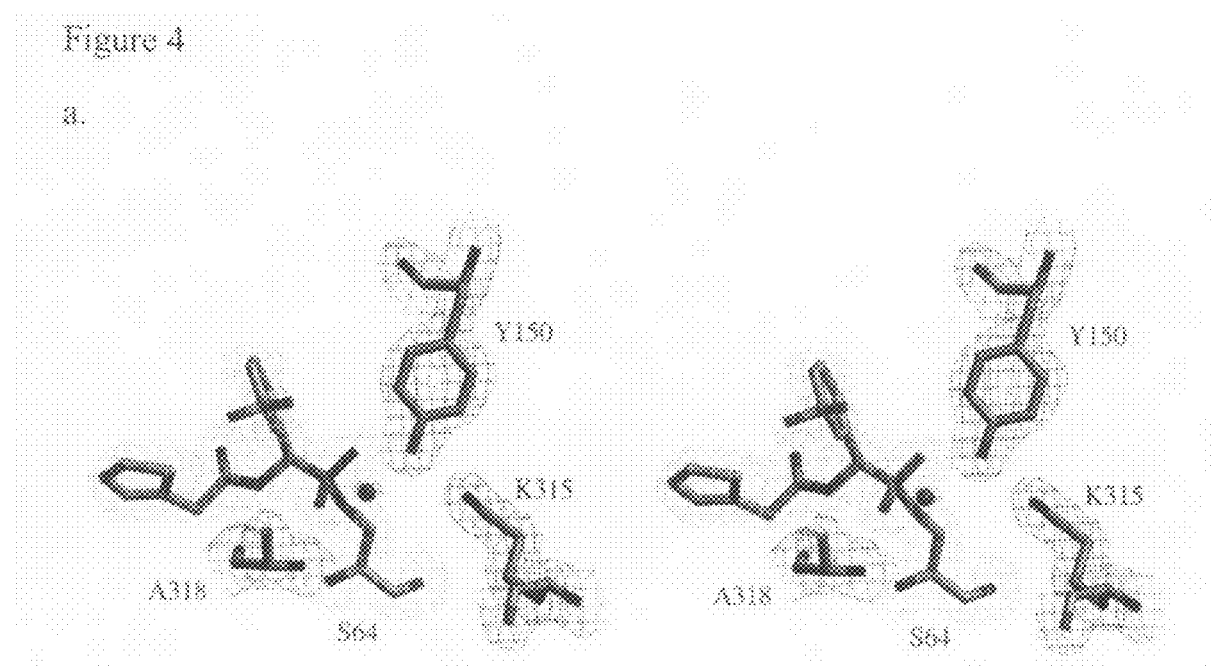
FIG. 4. Stereoview of 2|Fo|-|Fc| electron density maps of the refined model of AmpC in complex with (A) compound 16 and (B) compound 21, contoured at 1σ. The simulated-annealing omit electron density maps for the inhibitors are contoured at 3σ. The putative deacylating water Wat402 is shown as a sphere. The figures were generated using SETOR.
Figure 4:
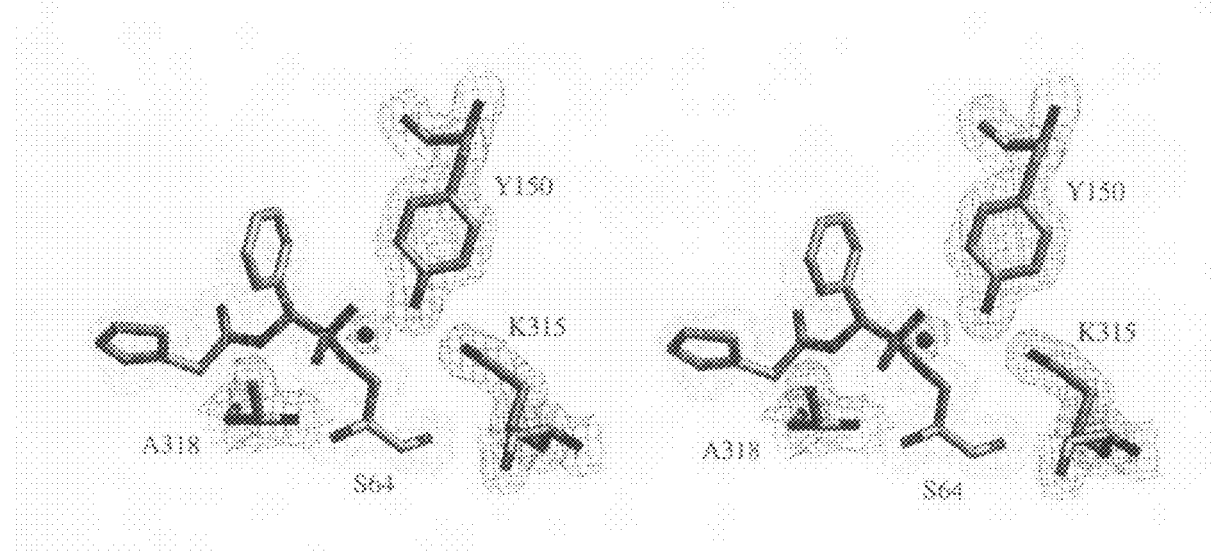
Figure 5:
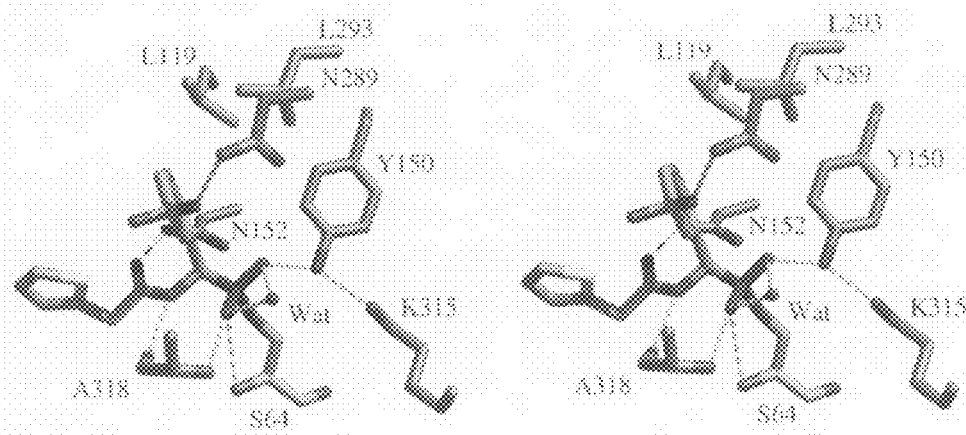
FIG. 5. Active site of AmpC in complex with (A) compound 16 and (B) compound 21. In (C), the complex of AmpC with 16 is overlaid with AmpC in complex with cephalothin (PDB entry 1KVL). Dashed lines represent key hydrogen bonds. Spheres represent water molecules. Interaction distances are listed in Table 3.
Figure 5:
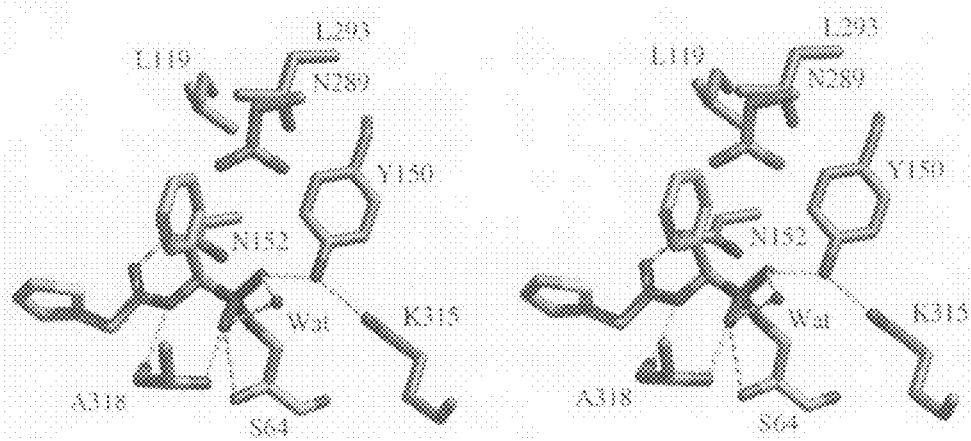
Figure 5:
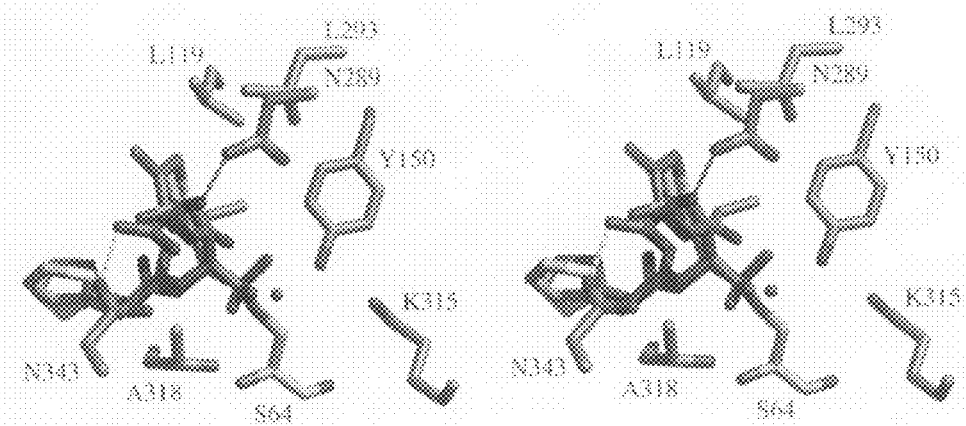

The position of the inhibitor in the active site was unambiguously identified in the initial |Fo|−|Fc| difference map contoured at 3σ. Electron density connected the Oγ of the catalytic Ser64 to the boron atom of the inhibitors (FIG. 4a). The boron geometry was tetrahedral as expected, and key hydrogen bond interactions in the active site closely resemble those typically observed in β-lactamase structures with transition state analogs and with β-lactams (FIG. 5a; Table 3). The O12 of the boronic acid is placed in the "oxyanion" or "electrophilic" hole formed by the backbone amide groups of Ser64 and Ala318 (Table 3). The O13 of the boronic acid interacts with the putative catalytic base Tyr150. Two well-ordered and highly conserved water molecules are also observed. Wat402, which appears to be the deacylating water, interacts with both O12 and O13 of the boronic acid (FIG. 5a). The second water molecule, Wat403, interacts with Wat402, the Oδ1 atom of Asn346 and the Nη1 atom of Arg349 (not shown). The amide group of the inhibitor is placed in the amide recognition region defined by Asn152 and Ala318. The nitrogen (N9) of the amide group interacts with the backbone oxygen of Ala318 and the carbonyl oxygen (O8) interacts with Nδ2 of Asn152. The benzene ring is in van der Waals contact with Leu119 and Leu293 (distances range from 3.6 to 4.5 Å for each leucine, respectively), which form a hydrophobic patch on AmpC Unexpectedly, the carboxylic acid group is observed to interact with N62 of Asn289 and two ordered water molecules, Wat181 and Wat469. Although canonical carboxylate binding residues, such as Thr316 and Asn346, are nearby, no direct interaction is observed to these residues.

TABLE 3

Interactions in inhibitorbound and native AmpC β-lactamase

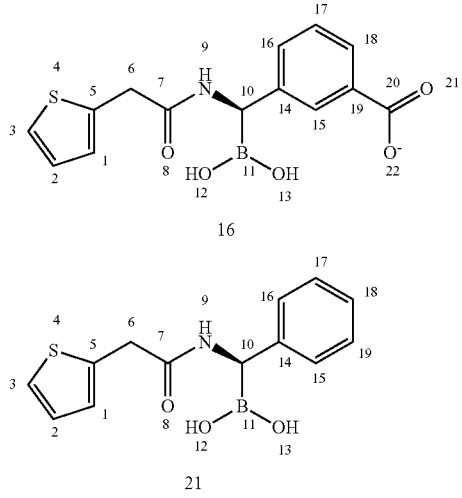

| Interaction | Distance (Å) | | |
|---|---|---|---|
| | AmpC/1 6[a] | AmpC/21[b] | Apo[b,c] |
| S64N-O12 | 3.1 | 3.2 | N.P.[d] |
| A318N-O12 | 2.7 | 2.8 | N.P. |
| A318O-O12 | 3.3 | 3.3 | N.P. |
| Y150OH-O13 | 2.7 | 2.7 | N.P. |
| Wat402-O12 | 2.8 | 3.0 | N.P. |
| Wat402-O13 | 3.0 | 2.9 | N.P. |
| Y150OH-K315Nξ | 2.9 | 2.9 | 2.5 |
| Y150OH-S64Oγ | 3.0 | 3.0 | 3.2 |
| Y150OH-K67Nξ | 3.3 | 3.2 | 3.1 |
| K67Nξ-A220O | 2.8 | 2.9 | 3.5 |
| K67Nξ-S64Oγ | 2.6 | 2.7 | 3.5 |
| Wat402-T316Oγ1 | 3.4 | 3.2 | 3.8 |
| Wat402-Wat403 | 2.6 | 2.7 | 2.9 |
| Wat403-N346 Oδ1 | 2.7 | 2.8 | 2.7 |
| Wat403-R349Nη1 | 3.0 | 3.1 | 2.9 |
| A318O-N9 | 3.1 | 3.2 | N.P. |
| N152Nδ2-O8 | 2.8 | 2.9 | N.P. |
| Q120Nε2-O8 | 6.5 | 2.9 | N.P. |
| N152Oδ1-K67Nξ | 2.6 | 2.6 | 2.7 |
| N152Nδ2-Q120Oε1 | 7.1 | 2.6 | 3.0 |
| Wat181-O22 | 3.0 | N.P. | N.P. |
| Wat469-O23 | 3.1 | N.P. | N.P. |
| N189Nδ2-O22 | 2.9 | N.P. | N.P. |

[a]Distances are for monomer 1 of the asymmetric unit.
[b]Distances are for monomer 2 of the asymmetric unit.
[c]The apo structure used as reference is PDB code 1KE4. Powers, R.A. and Shoichet, B.K.J. Med. Chem. 2002, 45, 3222-3234.
[d]Not present To investigate the role of this carboxylate, the derivative 21 was made, lacking the carboxylate but maintaining the phenyl ring. This compound was 35-fold less active than compound 16, which has the carboxylate (Table 1). Comparing the affinity of 21 ($K_i$ value of 35 nM) to the affinity of 16 ($K_i$ value of 1 nM) suggests that the carboxylate by itself contributes about 2.1 kcal/mol to the interaction energy with AmpC.

To understand this result, the crystal structure of AmpC in complex with 21 to 1.72 Å resolution was determined. Excluding proline and glycine residues, 92.5% of the amino acids were in the most favored regions of the Ramachandran plot (7.5% in the additionally allowed regions), with other crystallographic statistics consistent with a well-determined structure (Table 2). The position of the inhibitor in the active site was unambiguously identified in the initial |Fo|-|Fc| difference map contoured at 3σ. Electron density connected the Oγ of the catalytic Ser64 to the boron atom of the inhibitor; the boron geometry was tetrahedral as expected (FIG. 4b). The AmpC/21 complex resembles the AmpC/16 complex, making most of the same interactions, save for those involving the deleted carboxylate group (FIG. 5b, Table 3).

Microbiology. To investigate the potential of these compounds to reverse antibiotic resistance, preliminary antimicrobial activity studies in bacterial cell culture were performed. Reference is made to example 14, below. The minimum inhibitory concentration (MIC) of ceftazidime against eight clinically isolated bacterial pathogens producing class Cβ-lactamases ranged from 256 μg/ml to 32 μg/ml. Both 16 and 21 showed synergy with ceftazidime against all strains. Compound 16 was slightly more potent than compound 21, improving the MIC values of ceftazidime by between 8 and 32-fold (Table 4).

TABLE 4

Synergy of compounds 16 and 21 with ceftazidime against bacteria producing β-lactamase.

| | MIC[a] (μg/ml) | | |
|---|---|---|---|
| Strain | CAZ[b] | CAZ + 16[b,c] | CAZ + 21[b,c] |
| C. freundii | 256 | 8 | 8 |
| E. coli 1[d] | 32 | 1 | 4 |
| E. coli 2[d] | 256 | 16 | 16 |
| E. cloacae 1[d] | 256 | 8 | 8 |
| E. cloacae 2[d] | 32 | 4 | 8 |
| E. cloacae 3[d] | 256 | 16 | 16 |
| P. aeruginosa 1[d] | 256 | 16 | 32 |
| P. aeruginosa 2[d] | 64 | 8 | 8 |

[a]Minimum inhibitory concentration.
[b]CAZ = ceftazidime
[c]The ratio of ceftazidime to inhibitor was 1:1.
[d]Strains defined in Materials.

Selectivity. To investigate the selectivity of these compounds, 16 and 21 were tested against the serine proteases α-chymotrypsin, β-trypsin, and elastase (Table 5). Compound 16 was 57,000-fold more selective for AmpC over α-chymotrypsin and 190,000-fold more selective for AmpC over elastase. Compound 21 was 60-fold and 1,400-fold more selective for AmpC over α-chymotrypsin and elastase, respectively. Neither compound had any measurable activity against β-trypsin below 1 mM. Reference is made to example 12, below.

TABLE 5

Selectivity of 16 and 21 for AmpC versus serine proteases.

| Enzyme | $IC_{50}$ (μM) for 16 | $IC_{50}$ (μM) for 21 |
|---|---|---|
| AmpC | 0.0026 | 0.090 |
| α-Chymotrypsin | 150 | 6.0 |

TABLE 5-continued

Selectivity of 16 and 21 for AmpC versus serine proteases.

| Enzyme | IC$_{50}$ (μM) for 16 | IC$_{50}$ (μM) for 21 |
| --- | --- | --- |
| β-Trypsin | >>1000 | >>1000 |
| Elastase | 500 | 128 |

As described herein, representing the broader utility of the present invention, the high affinity of compound 16, which inhibits AmpC β-lactamase with a K, value of 1 nM, is illustrated in Table 1. This is a 300-fold improvement over the prior art compound 4 (Table 1), which lacks the m.carboxyphenyl group. This result supports the view that a C3(4)' acidic group, which is ubiquitous among β-lactams, is a key recognition feature in AmpC Although this is well accepted for the class A β-lactamases, the contribution of the β-lactam carboxylate to recognition by the class C enzymes has been uncertain.

In order to determine what enzyme groups are responsible for complementing this functionality, the structure of the complex between AmpC and compound 16 was determined by x-ray crystallography (FIG. 5a, Table 2). It was expected that the carboxylate of 16 would interact with Asn346 or Thr316, which both crystallography and mutagenesis studies suggest are responsible for interacting with the C3(4)' carboxylates of penicillins and cephalosporins. Instead, the carboxylate hydrogen bonded with the nearby Asn289 and two ordered water molecules new to this structure (FIGS. 5a and 5c; Table 3). Asn289, though in the active site region, has not previously been implicated as a functional residue in AmpC and is only modestly conserved among class C β-lactamases (although in most species of AmpC a polar residue is found at this position).

As illustrated in Table 3, the phenyl ring of the m.carboxyphenyl group formed van der Waals interactions with the hydrophobic patch on AmpC made up of Leu119 and Leu293, previously found to be a hot-spot for ligand interactions in the enzyme.

To investigate whether the carboxylate was really driving affinity and not some other group, compound 21, the analog of 16 that retains the phenyl ring but replaces the m.carboxylate with a hydrogen was synthesized (Table 3). If the phenyl ring were responsible for most of the 3.4 kcal/mol improvement in interaction energy, it would be expected that the affinity of this analog would resemble that of 16. Instead, it lost 35-fold activity compared to 16, suggesting that the carboxylate is responsible for most of the affinity gain (Table 1). The structure of the AmpC/21 complex, determined by x-ray crystallography to 1.72 Å, shows that the two compounds bind similarly in the AmpC site and that no significant enzyme rearrangement has occurred between the two complexes.

Figure 6:
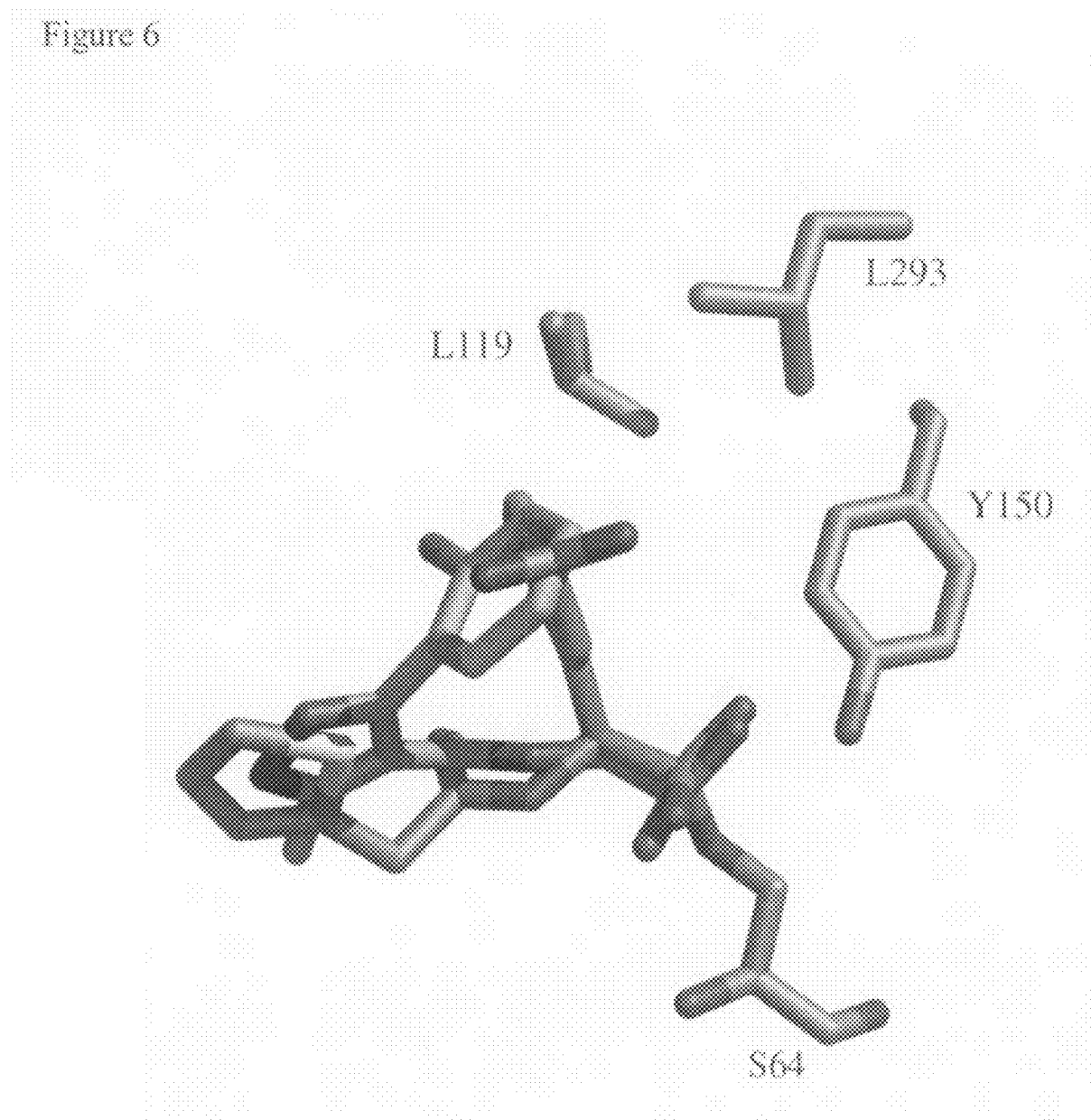

Thus, without restriction to any one theory or mode of operation, the carboxylate is believed to be a recognition feature for AmpC. Since the phenylglycylboronic acids are reversible inhibitors, an energetic value can be assigned to this functional group: 2.1 kcal/mol. This is a large value, considering the need to desolvate the carboxylate, though not unprecedented for a polar-ionic interaction. The evidence suggests, therefore, that such a functionality contributes significantly to binding of this inhibitor (2.1 kcal/mol), and by extension to recognition of β-lactam substrates by class Cβ-lactamases. Conversely, Table 1 illustrates that the m.carboxyphenylglycylboronic acid 17 is a lessor inhibitor, nearly 40-fold worse than glycylboronic acid 2, the latter of which lacks the carboxylate. An overlay of the crystal structures of the AmpC complex with the glycylboronic acid 2 and that of AmpC/16 explains this unanticipated drop in affinity (FIG. 6). The bulky R1 side chains of 2 and 17, which bend back toward the boronic acid group, will sterically clash with the introduced m.carboxyphenyl moiety in 17, disrupting its interactions with the enzyme; this would also be true of 14. The inability to even synthesize the m.carboxyphenylglycylboronic acid 14, presumably also reflects this crowding. Such observations may suggest, in designing transition-state analogs for β-lactamases, the two side chains, each of which individually can contribute significantly to binding, should be—in certain embodiments—sterically consistent with one another.

Even with this caveat, compounds of this family have several attractive features. Compound 16 is highly selective for AmpC, having little affinity for serine proteases such as chymotrypsin (Table 5). This high level of selectivity may reflect the hydrophilicity of compound 16 and its chiral display of relatively dense functionality. Whereas the activity of these compounds in cell culture (Table 4) is several orders of magnitude worse than their activity as enzyme inhibitors, they are nevertheless relatively potent at reversing the resistance of clinical pathogens such as E. cloacae, which are currently such a problem in hospitals.

Although it is clear from the structure of 16/AmpC that the benzoic acid hydrogen bonds with Asn289 and makes hydrophobic contacts with both Leu119 and Leu293, the energies of these interactions are unknown. For instance, the carboxylate improves 16's binding energy by 2.1 kcal/mol, but it is unclear how much of this energy owes directly to the hydrogen bond between the carboxylate and Asn289, or to more general interactions with the residues in the carboxylate binding site (FIG. 5c). It is possible that this binding energy could alternatively result from ionic interactions between the carboxylate and positively charged protein residues, or through hydrogen bonds with ordered water molecules. Thus, quantitative knowledge of the energy of these interactions can assist to in design of future derivatives of 16, as those interactions critical to the high affinity of the lead compound should be preserved in any future iteration.

Figure 8:
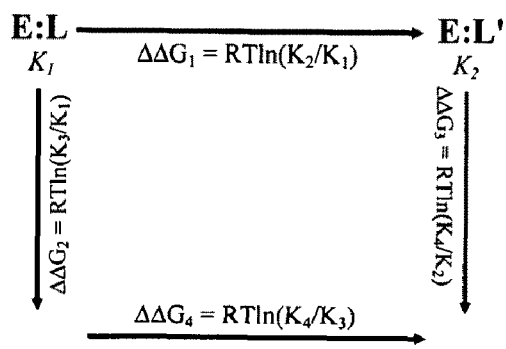
FIG. 8. General double perturbation thermodynamic cycle. E=wild-type enzyme, E'=mutant enzyme. L=wild-type ligand, L'="mutant" ligand. $\Delta\Delta\Delta G=(\Delta\Delta G_1-\Delta\Delta_4)$ or $(\Delta\Delta G_2-\Delta\Delta G_3)$.

Thermodynamic Cycle Analysis. One way to quantify the interaction energy is through the use of thermodynamic cycles. Such cycles can be used through double mutant perturbations to study the direct interactions between individual amino acids during protein folding, enzyme catalysis, protein-protein binding, and ion channel function. Similarly, it is possible to use thermodynamic cycles to study the interaction between a functional group of a ligand and an active site residue. These experiments use wild-type and "mutant" versions of both the enzyme and ligand, with each "mutant" lacking the interacting groups of interest. The energetic cost, ΔΔG, of removing the ligand functional group both in the presence and the absence of the residue with which it interacts can be calculated, and the difference between these energies, ΔΔΔG, is the energy of the interaction (FIG. 8). In these experiments, analog ("mutant") forms of the ligand must be synthesized, and for drug-like organic molecules this is rarely as straight forward as making a site substitution in a protein. This might explain why this sort of analysis is rarely used in drug-design efforts, even though it is the surest path to understanding what interactions are important for affinity.

Figure 7A:
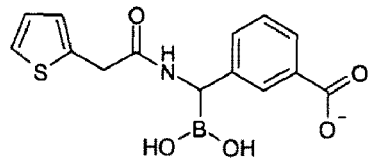
FIG. 7. Comparison of (A) compound 16, a 1 nM inhibitor of AmpC, (B) compound 21, a 35 nM inhibitor of AmpC, (C) compound 4, a 186 nM inhibitor of AmpC, and (D) compound 26, a 15 nM inhibitor of AmpC.
Figure 7B:
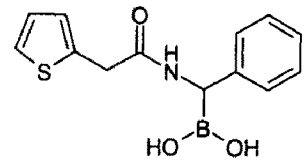
Figure 7C:
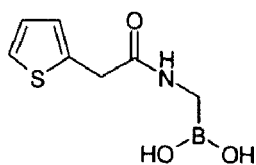
Figure 9A:
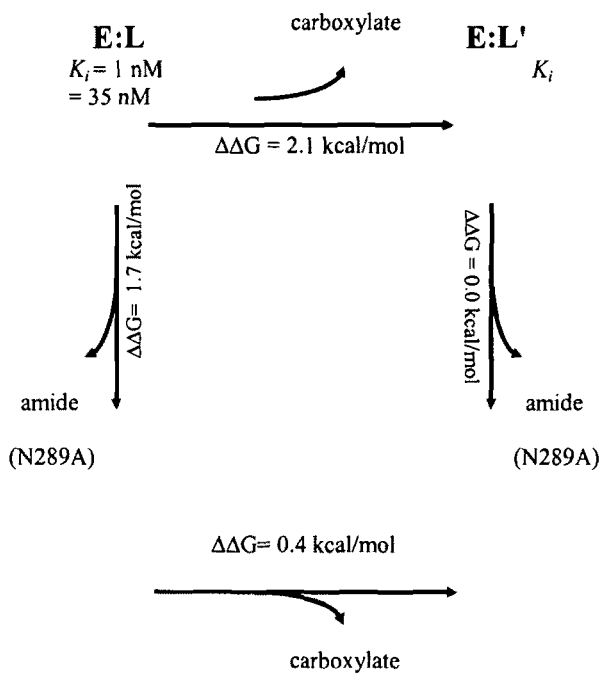
FIG. 9. (A) Thermodynamic cycle to quantify the hydrogen bond energy between Asn289 and the inhibitor carboxylate. E=wild-type AmpC, E'=AmpC N289A. L=compound 16, L'=compound 21. $\Delta\Delta\Delta G$=1.7 kcal/mol. (B) Thermodynamic cycle to quantify the interaction between the inhibitor phenyl ring and Leu119. E=wild-type AmpC, E'=AmpC L119A. L=compound 21, L'=compound 4. $\Delta\Delta\Delta G$=−1.4 kcal/mol. (C) Thermodynamic cycle to quantify the interaction between the inhibitor phenyl ring and Leu293. E=wild-type AmpC, E'=AmpC L293A. L=compound 21, L'=compound 4. $\Delta\Delta\Delta G$=−0.5 kcal/mol.
Figure 9B:
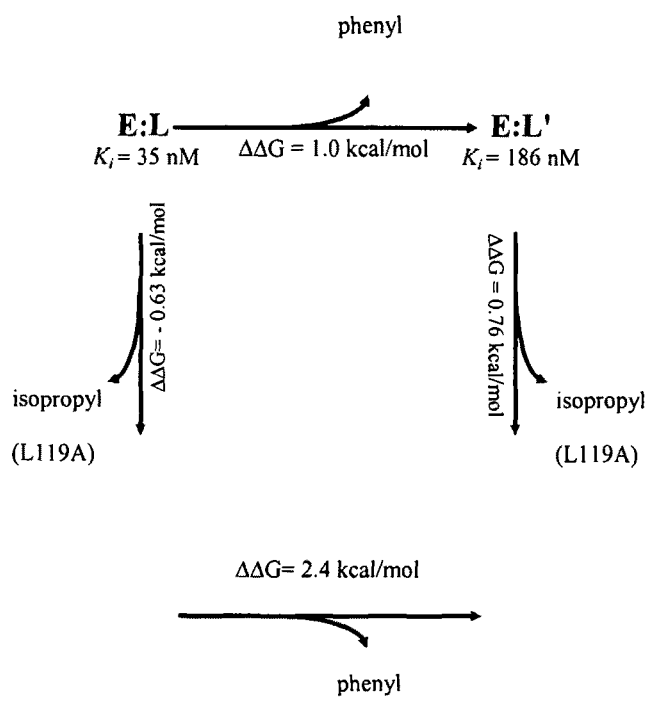
Figure 9C:
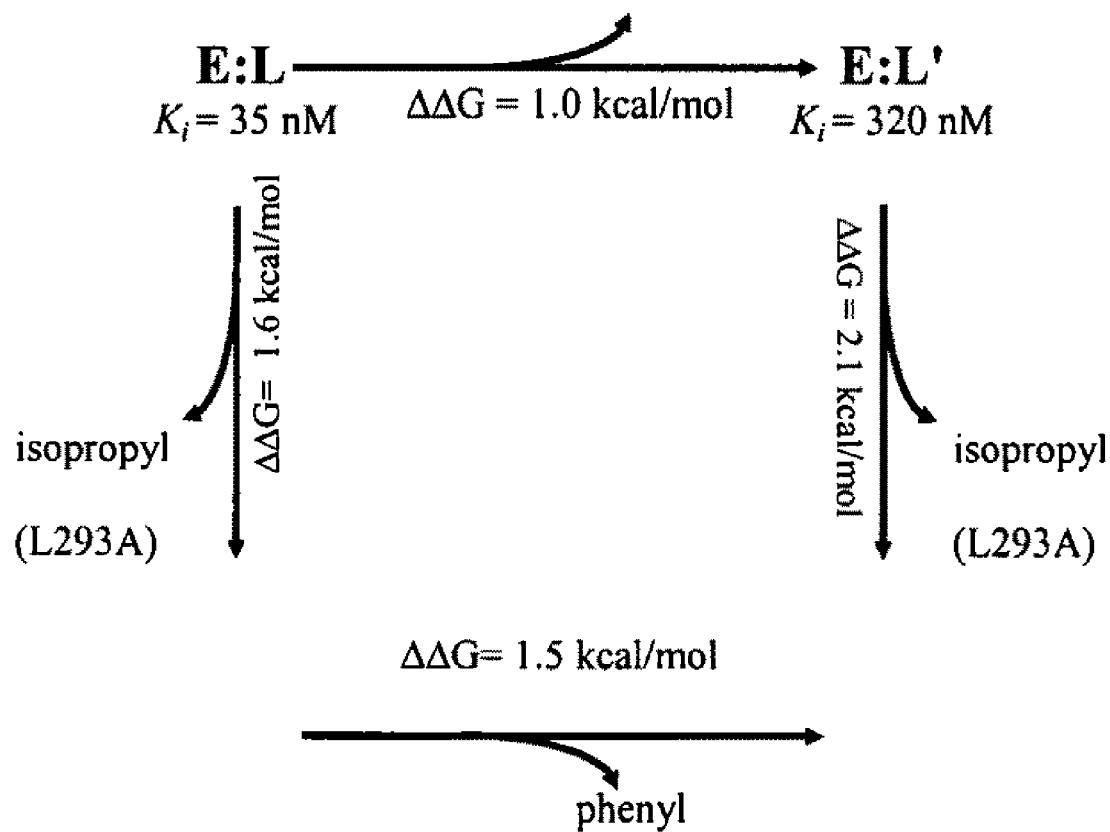

To quantify the energetic contributions of the hydrogen bond with Asn289 and the hydrophobic contacts with Leu119 and Leu293, three separate double-perturbation thermodynamic cycles were prepared (Reference is made to compounds 16, 21, 4; FIG. 7a-7c). K$_i$ values for all four possible enzyme-ligand combinations were used to calculate ΔΔG values for transitions between each complex. To determine the energy of the hydrogen bond, the thermodynamic cycle A was set up with 16 as the "wild-type" ligand, and 21 as the "mutant" ligand (FIG. 9a). In this cycle, AmpC N289A was used as the mutant enzyme. To determine the energies of the phenyl ring interactions with both Leu119 and Leu293, two separate thermodynamic cycles B and C were set up with AmpC L119A and L293A as the respective mutant enzymes (FIGS. 9b and 9c). In both of these cycles, 21 was considered the "wild-type" ligand, and 4 the "mutant" ligand. To give these energetic studies a detailed structural context, X-ray crystal structures of N289A in complex with both 16 and 21 were determined to 1.49 Å and 1.39 Å, respectively.

Three mutant AmpC enzymes were created to quantify interaction energies: Asn289→Ala, Leu119→Ala, and Leu293→Ala. These substitutions were chosen to eliminate the interactions with the carboxylate and the phenyl ring of 16, respectively, while minimizing the chance of introducing new interactions or perturbing the enzyme. All three mutant enzymes could be expressed and purified, though yields for L119A and L293A were lower than typical for wild-type (Table 6). In the case of N289A, the relative stability of the folded enzyme, as determined by thermal denaturation using CD spectropolarimetry, was nearly identical to that of wild-type (data not shown). All three enzymes retained substantial activity against β-lactam substrates such as nitrocefin. Both the "wild-type" and "mutant" inhibitors were tested against the corresponding enzymes of their respective thermodynamic cycles and K, values were determined (Table 6). Reference is made to examples 16 and 17, below.

TABLE 6

$K_i$ values for inhibitors 4, 16, 21, 26.

| Enzyme | Inhibitor | $K_i$ (nM) |
| --- | --- | --- |
| WT AmpC | 16 | 1* |
| WT AmpC | 21 | 35* |
| WT AmpC | 4 | 186 |
| WT AmpC | 26 | 15 |
| AmpC N289A | 16 | 17 |
| AmpC N289A | 21 | 37 |
| AmpC N289A | 26 | 18 |
| AmpC L119A | 21 | 12 |
| AmpC L119A | 4 | 676 |
| AmpC L293A | 21 | 521 |
| AmpC L293A | 4 | 6200 |

The energy of the hydrogen bond between Asn289 and the carboxylate of compound 16 was investigated using the mutant enzyme N289A. This substitution reduced the affinity of 16 by 17-fold versus the wild-type enzyme (Table 6). The affinity of compound 21, the de-carboxy analog of 16 (FIG. 7b), falls 35-fold for the wild-type enzyme relative to the affinity of 16, but only falls 2-fold for N289A relative to the affinity of 16 for the mutant. Construction of a double-"mutant" cycle reveals that the hydrogen bond between the carboxylate of 16 and the amide of Asn289 contributes 1.7 kcal/mol of net binding energy to the complex (FIG. 9a). Similarly, the energy of the apparent non-polar interaction between the phenyl ring of 21, and by extension 16, and the hydrophobic patch made up of Leu119 and Leu293 was investigated by the mutant enzymes L119A and L293A. Unexpectedly, the affinity of 21 for L119A was actually better than for the wild-type enzyme. Completion of the thermodynamic cycle by measuring the affinity of compound 4, the achiral analog of 21 that lacks the phenyl ring, gives a net interaction energy between the phenyl ring and L119 of −1.4 kcal/mol—i.e., this is an unfavorable interaction (FIG. 9b). Although the L293→Ala substitution does reduce the affinity for 21 by 1.6 kcal/mol, completing the same thermodynamic cycle suggests that here too the interaction with the phenyl ring is unfavorable, if only by −0.5 kcal/mol (FIG. 9c).

Figure 7D:
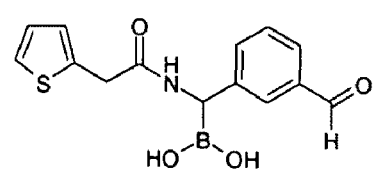

Without limitation to any particular theory, the relatively high magnitude of the hydrogen bond between Asn289 and the carboxylate of 16 may be attributed to its ion-dipole character. Since the cost of desolvating the inhibitor carboxylate would be expected to be high, the affinity of a neutral hydrogen bond acceptor was investigated. The aldehyde analog of 16, compound 26 (FIG. 7d), was synthesized. The affinity for wild-type AmpC was reduced 15-fold relative to that of 16, whereas there was a negligible reduction in the affinity of 26 for N289A relative to that of 16. Thermodynamic cycle analysis reveals that the hydrogen bond between Asn289 and the aldehyde is negligible. This is an example of an interaction where, notwithstanding the desolvation costs, an ionic interaction contributes significantly not only to specificity but also affinity.

Figure 10A:
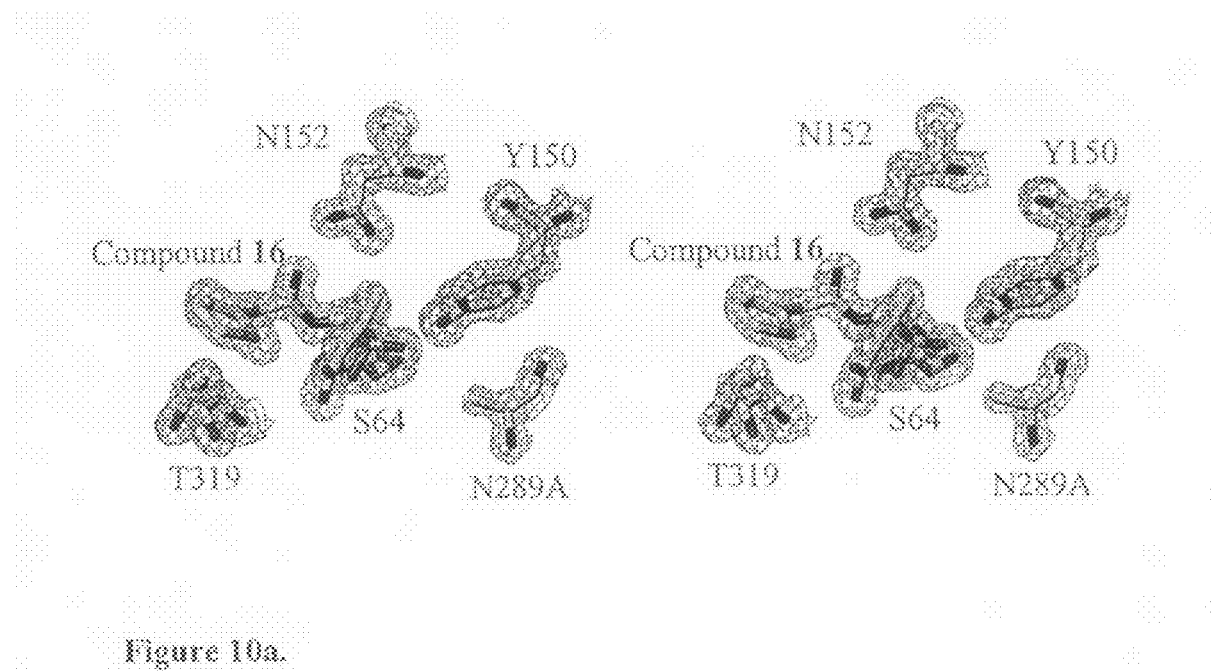
FIG. 10. (A) Simulated annealing omit electron density of compound 16 in complex with N289A. The $F_o-F_c$ electron density is contoured at 4σ. The $2F_o-F_c$ electron density is contoured at 1σ. (B) Simulated annealing omit density of compound 21 in complex with N289A. The $F_o-F_c$ electron density is contoured at 4σ. The $2F_o-F_c$ electron density is contoured at 1σ.
Figure 10B:
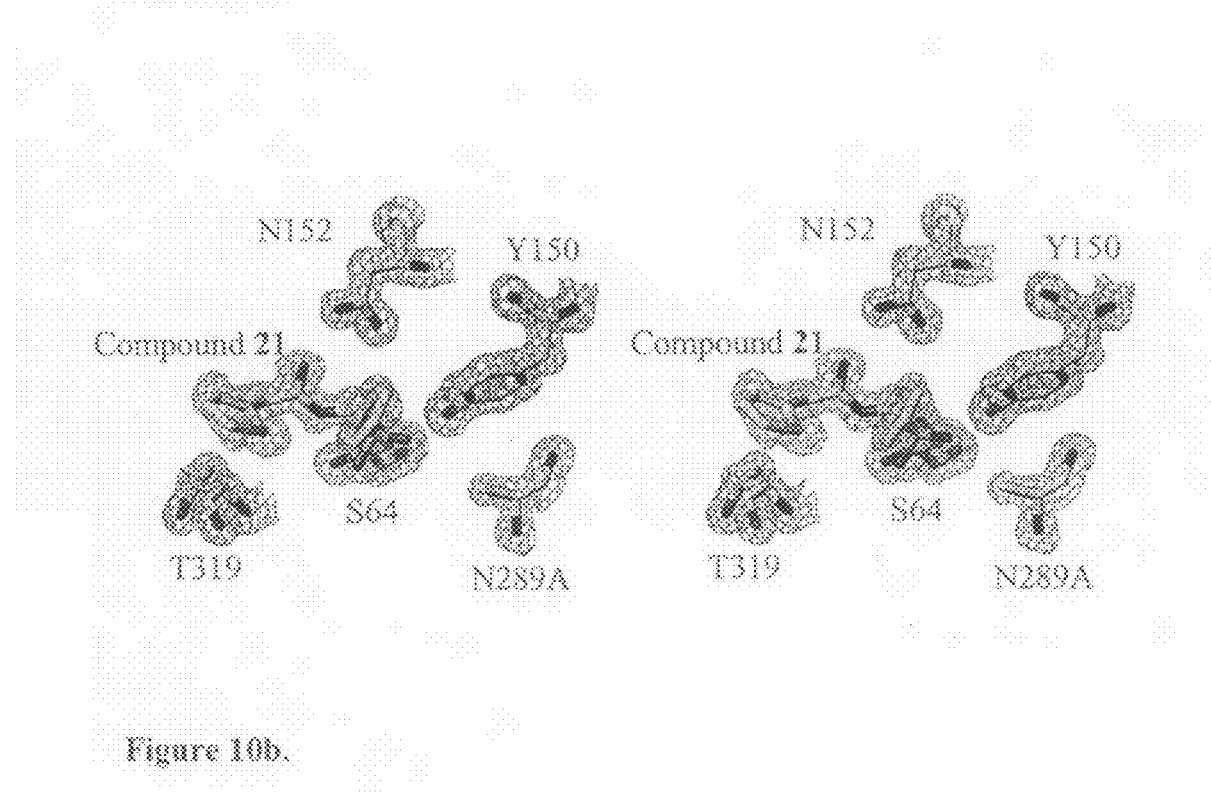
Figure 11A:
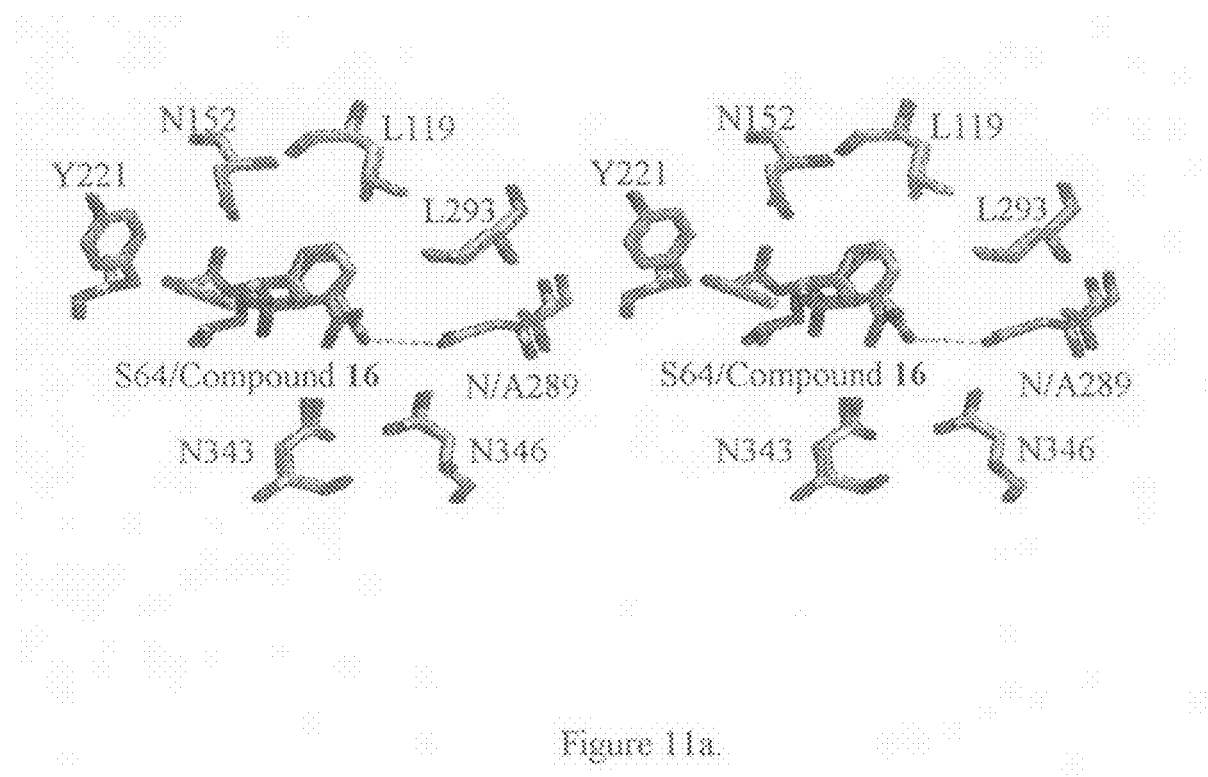
FIG. 11. Overlay of wild-type and mutant enzyme complexes with compounds 16 and 21. (A) Structures of 16/WT AmpC and 16/N289A. (B) Structures of 21/WT AmpC (10) and 21/N289A.
Figure 11B:
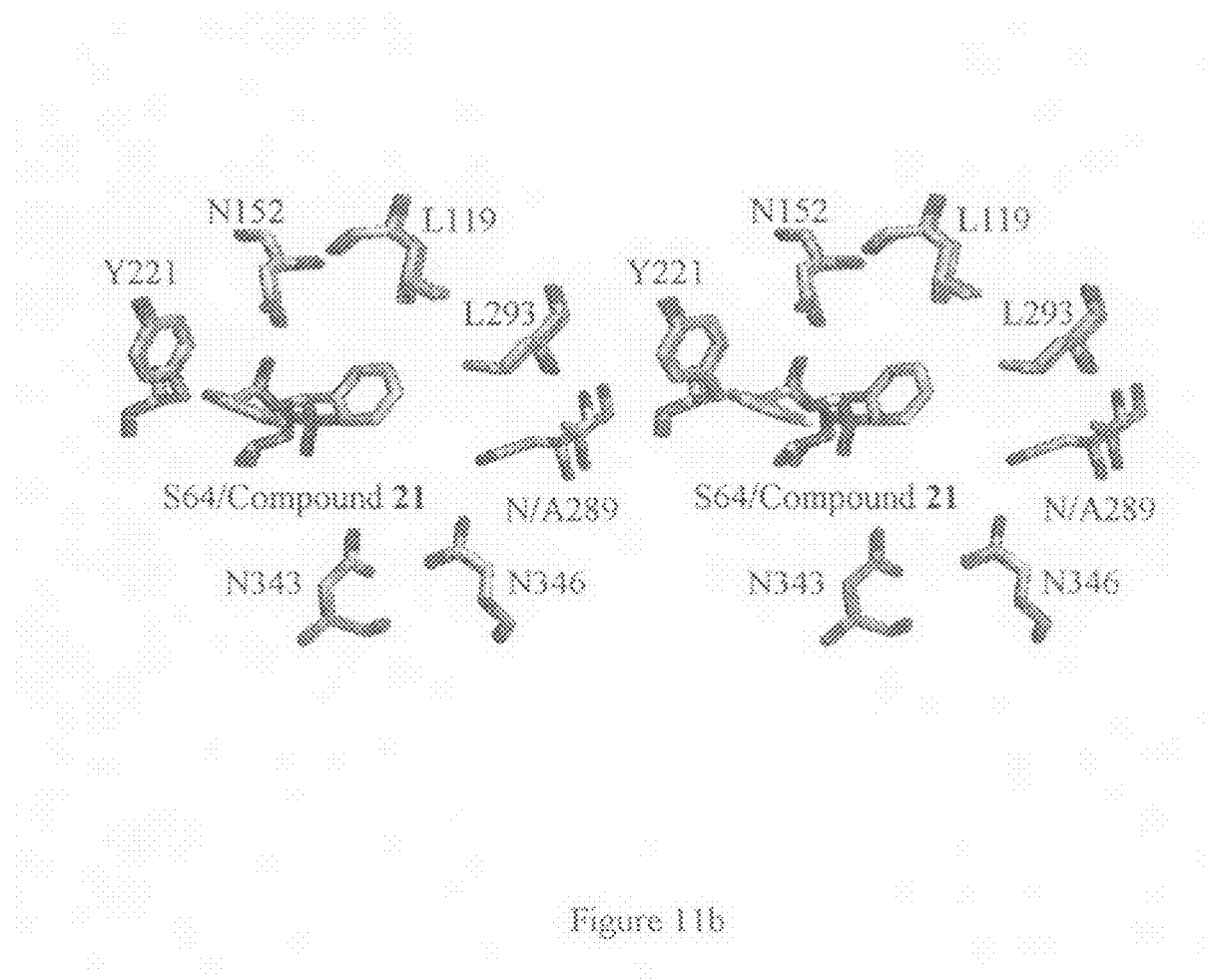

To understand the structural context of the hydrogen bond energy, the structures of the complexes of 16/N289A and 21/N289A were determined by X-ray crystallography to 1.48 Å for 16/N289A and to 1.39 Å for 21/N289A (Table 7). The two structures were refined to $R_{cyst}/R_{free}$ values of 15.6/16.9% and 15.9/17.3%, respectively, and the overall statistics suggest well determined structures (Table 7). The location of the inhibitors in the mutant enzyme, as well as the presence of the mutation itself, was determined by unambiguous simulated annealing omit electron density (FIGS. 10a and 10b). For both structures, 100% of the amino acids were either in the most favored regions or the additionally allowed regions of the Ramachandran plots (proline and glycine residues excluded). The interactions between the inhibitors and the enzyme are nearly identical to those between the inhibitors and wild-type AmpC, with the obvious exception of the lost hydrogen bond between the m-carboxylate of 16 and residue 289, now substituted by an alanine (Table 8). Overlays of the active sites of these two complexes with the corresponding wild-type complexes demonstrate a close match (FIGS. 11a and 11b), indicating that there has been no significant reorganization of the active site in the mutant enzyme. Reference is made to example 18, below.

TABLE 7

Crystallography statistics.

| Statistics | Complex | |
| --- | --- | --- |
| | N289A/16 | N289A/21 |
| cell constants (Å; deg) | a = 119.05; | a = 118.63; |
| | b = 76.01; | b = 76.10; |
| | c = 97.60; | c = 97.84; |
| | β = 115.54 | β = 115.62 |
| space group | C2 | C2 |
| resolution range (Å) | 15.0-1.49 | 20.0-1.39 |
| | (1.54-1.49)[a] | (1.45-1.39)[a] |
| unique reflections | 128,092 (12,767) | 156,947 (15,495) |
| total observations | 483,237 | 903,131 |
| $R_{merge}$ (%) | 5.1 (18.4) | 5.8 (13.4) |
| completeness (%) | 99.9 (100.0) | 99.4 (98.3) |

TABLE 7-continued

Crystallography statistics.

| Statistics | Complex | |
|---|---|---|
| | N289A/16 | N289A/21 |
| $<I>/<\sigma(I)>$ | 23.8 (7.6) | 29.0 (10.4) |
| number of protein residues | 716 | 716 |
| number of water molecules | 1179 | 1047 |
| RMSD bond lengths (Å) | 0.011 | 0.013 |
| RMSD bond angles (deg) | 1.61 | 1.71 |
| $R_{cryst}$ (%) | 15.6 | 15.9 |
| $R_{free}$ (%) | 16.9 | 17.3 |
| average B-factor, protein atoms (Å$^2$) | 14.5[b] | 14.2[b] |
| average B-factor, inhibitor atoms (Å$^2$) | 19.8[b] | 15.3[b] |
| average B-factor, water molecules(Å$^2$) | 31.8 | 29.0 |

[a]Values in parenthesis are for the highest resolution shell.
[b]Values cited were calculated for the B-monomer of the asymmetric unit.

TABLE 8

Key enzyme-inhibitor and active site interactions observed in the crystal structures.

Compound 16

Compound 21

| interaction | Distance (Å) | | | |
|---|---|---|---|---|
| | 16/N289A | 16/WT AmpC* | 21/N289A | 21/WT AmpC* |
| S64N-O12 | 3.2 | 3.1 | 3.1 | 3.2 |
| A318N-O12 | 2.8 | 2.7 | 2.8 | 2.8 |
| A318O-O12 | 3.2 | 3.3 | 3.2 | 3.3 |
| Y150OH-O13 | 2.6 | 2.7 | 2.6 | 2.7 |
| Wat402-O12 | 3.0[†] | 2.8 | 3.1[‡] | 3.0 |
| Wat402-O13 | 2.8[†] | 3.0 | 2.9 | 2.9 |
| Y150OH-K315Nξ | 2.9 | 2.9 | 2.9 | 2.9 |
| Y150OH-S64Oγ | 3.1 | 3.0 | 3.1 | 3.0 |
| Y150OH-K67Nξ | 3.3 | 3.3 | 3.2 | 3.2 |
| K67Nξ-A220O | 2.9 | 2.8 | 2.9 | 2.9 |
| K67Nξ-S64Oγ | 2.8 | 2.6 | 2.8 | 2.7 |
| Wat402-T316Oγ1 | 3.1[†] | 3.4 | 3.11 | 3.2 |
| Wat402-Wat403 | 2.9[†] | 2.6 | 2.8 | 2.7 |
| Wat403-N346Oδ1 | 2.7 | 2.7 | 2.6 | 2.8 |
| Wat403-R349Nη1 | 3.0 | 3.0 | 3.1 | 3.1 |
| A318O-N9 | 3.1 | 3.1 | 3.1 | 3.2 |
| N152Nδ2-O8 | 2.9 | 2.8 | 2.9 | 2.9 |
| Q120Nε2-O8 | 3.5 | 6.5 | 3.4 | 2.9 |
| N152Oδ1-K67Nξ | 2.7 | 2.6 | 2.7 | 2.6 |
| N152Nδ2-Q120Oε1 | 3.0 | 7.1 | 3.1 | 2.6 |
| Wat181-O22 | 2.4 | 3.0 | NP | NP |
| Wat469-O23 | NP | 3.1 | NP | NP |
| N289Nδ2-O22 | NP | 2.9 | NP | NP |

*From Morandi, 2003.
[†]Denotes value for one of two conformations of equal occupancy.
[‡]Denotes value for conformation with highest occupancy.
NP: not present.

Synthesis of compounds 16 and 21 are as previously described above. As detailed below, with reference to Scheme 3 and examples 20 and 21, below, the synthesis of compound 26 is described. (+)-pinanediol (1R)-1-acylamino-1-(3-formylphenyl)methylboronates 25, 26 were obtained starting from commercial 2-(3-bromo-phenyl)-[1,3]dioxolane (22a), following the same procedure. Metallation of 22a with buthyllithium at −78° C., followed by reaction with trimethylborate and transesterification with (+)-pinanediol, afforded the desired (+)-pinanediol (3-[1,3]dioxolan-2-yl-phenyl)boronate (+)-23a together with variable amount of (+)-pinanediol (3-dimethoxymethyl)phenylboronate (+)-23b, this latter probably formed by transacetalization with the in situ formed methanol. To avoid this problem, 22a was converted to 22b (88%) and subsequently boronated to (+)-23b (75%).

Boronate (+)-23b was converted to compound 24 employing the described procedure for Matteson homologation. (+)-Pinanediol as chiral auxiliary is known to guide the stereochemical course of the homologation reaction affording the α-chloro derivative 24 in the desired S configuration. To prevent epimerization, this compound was used for the next step without purification and rapidly converted to the acylamino boronic ester in a one-pot procedure that involved substitution with bis-trimethylsilyl-lithium amide, acylation (acetic anhydride or thienyl acetyl chloride) and aldehyde deprotection (10-12% overall yield from 23b). Compound (1R)-(−)-25 and (1R)-(+)-26 showed $^1$H and $^{13}$C NMR, IR, mass spectra and elemental analyses in close agreement with the desired structures; high diastereoisomeric purity (de >98%) was displayed by diagnostic signals in $^1$H NMR analysis.

Scheme 3.
Steps in the synthesis of compound 26.

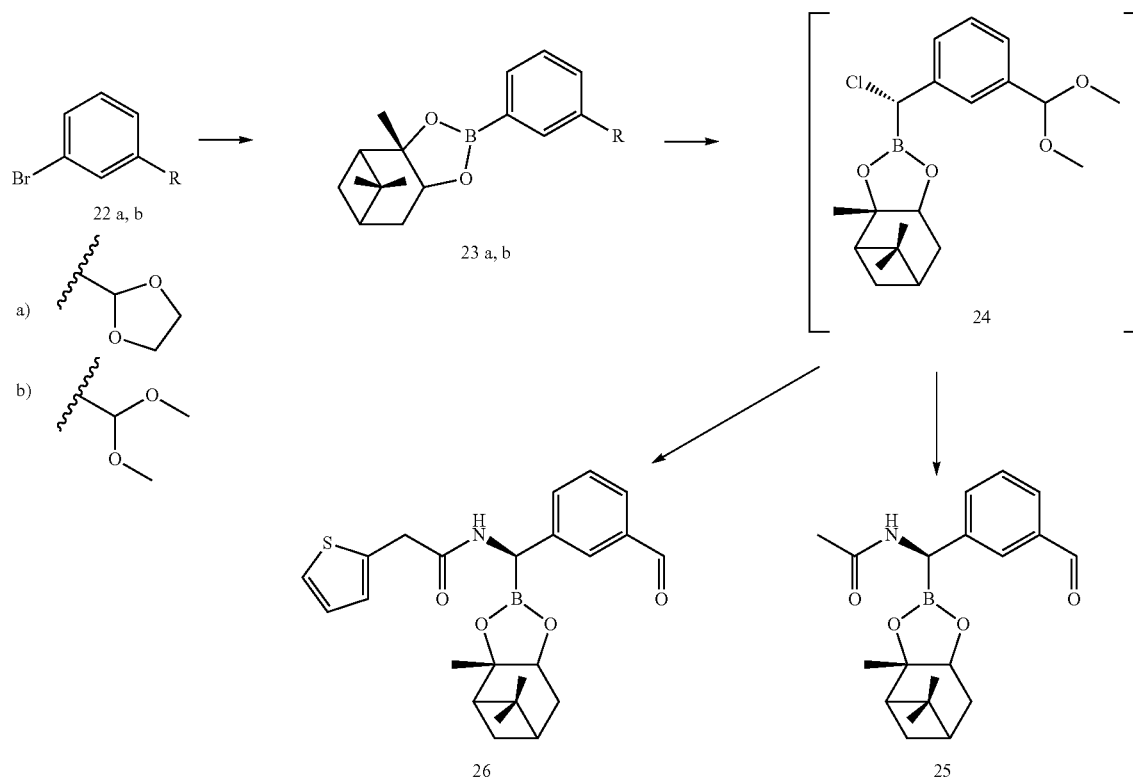

An interesting result to emerge from these studies is the large magnitude of the interaction energy between the amide of Asn289 and the carboxylate of the inhibitor 16. The 1.7 kcal/mol contributed by this hydrogen bond to overall affinity is within the range observed for ion-dipole hydrogen bonds between substrate groups and conserved recognition residues in enzymes. The effect of the ionic character of this interaction, as attested to by the effect of compound 26, is less expected; it is an example of a charged group contributing not only to specificity but also affinity, notwithstanding the desolvation cost. What is most surprising is that Asn289 is not a conserved recognition residue among the class C β-lactamases, nor is it known to play an important role in substrate recognition. Thus, whereas the energy that this interaction contributes to binding may be justified biophysically, its origins may in some sense be a manifestation of sequence variation in AmpC.

The thermodynamic cycles probing the interactions between the phenyl ring of 16 and the leucine patch on AmpC (FIGS. 9b and 9c) can be used, optionally, to guide future inhibitor design. Structural and computational studies suggest that this exposed hydrophobic patch is a good target for inhibitor groups to complement. Based on the observation that the phenyl ring in 16 and 21 are in close contact with this patch in the enzyme complexed structures determined by crystallography, it was expected that the interaction between the inhibitor and residues would be favorable. In fact, it is not. Although having a phenyl ring in 16 and 21 improves binding, this may not owe to interactions with residues with which it interacts most closely. Without limitation to any particular theory, an explanation for this may be that the phenyl ring is interacting with other nearby residues, such as Gln120, which appears to form a quadrupole-dipole interaction with the phenyl ring, or that the hydrophobicity of the phenyl ring is largely responsible for its contribution to affinity, suggesting that the identity of such a hydrophobic group can vary providing it provides at least in part a spacer function, for delivering the carboxylate or analogous anion to the active site.

In part, in accordance with the preceding, the present invention also provides a method of inhibiting a class A or class C β-lactamase or reversing such β-lactamase activity. Such a method comprises contacting the β-lactamase with an effective amount of an inventive compound or a pharmaceutically-acceptable derivative or salt thereof. The method can also include providing a β-lactam antibiotic, in addition to such compound.

In part, the present invention also provides a method of treating a class A or class C β-lactam antibiotic resistant bacterial infection. Such a method comprises administering to an animal or a mammal having such an infection, an effective amount of the inventive compound or a pharmaceutically-acceptable derivative or salt thereof. Accordingly, the present invention further provides one or more pharmaceutical compositions. Such a composition comprises a pharmaceutically-acceptable carrier, a compound of the present invention or a pharmaceutically-acceptable salt or derivative thereof and, optionally, a β-lactam antibiotic.

The compounds of this invention may contain an acidic or basic functional group and are, thus, capable of forming pharmaceutically-acceptable salts with pharmaceutically-acceptable acids and bases. The term "pharmaceutically-acceptable salts" refers to the relatively non-toxic, inorganic and organic acid and base addition salts of such compounds. These salts can be prepared by reacting the purified compound with a suitable acid or base. Suitable bases include the hydroxide, carbonate or bicarbonate of a pharmaceutically-acceptable metal cation, ammonia, or a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. Representative acid addition salts include the hydrobromide, hydrochloride, sulfate, phosphate, nitrate, acetate, valerate, oleate, palmitate, stearate, laurate, benzoate, lactate, phosphate, tosylate, citrate, maleate, fumarate, succinate, tartrate, napthalate, mesylate, glucoheptonate, lactobionate, and laurylsulphonate salts and the like.

As mentioned above, the compounds of this invention, and the pharmaceutically-acceptable salts thereof, are inhibitors of β-lactamases. Assays for the inhibition of β-lactamase activity are well known in the art. For instance, the ability of a compound to inhibit β-lactamase activity in a standard enzyme inhibition assay may be used (see, e.g., Example 1 below and M. G. Page, *Biochem J.* 295 (Pt. 1) 295-304 (1993)). β-lactamases for use in such assays may be purified from bacterial sources or, preferably, are produced by recombinant DNA techniques, since genes and cDNA clones coding for many β-lactamases are known. See, e.g., S. J. Cartwright and S. G. Waley, *Biochem J.* 221, 505-512 (1984). Alternatively, the sensitivity of bacteria known, or engineered, to produce a β-lactamase to an inhibitor may be determined. Other bacterial inhibition assays include agar disk diffusion and agar dilution. See, e.g., W. H. Traub & B. Leonhard, *Chemotherapy* 43, 159-167 (1997). Thus, a β-lactamase can be inhibited by contacting the β-lactamase enzyme with an effective amount of an inventive compound or by contacting bacteria that produce the β-lactamase enzymes with an effective amount of such a compound so that the β-lactamase in the bacteria is contacted with the inhibitor. The contacting may take place in vitro or in vivo. "Contacting" means that the β-lactamase and the inhibitor are brought together so that the inhibitor can bind to the β-lactamase. Amounts of a compound effective to inhibit a β-lactamase may be determined empirically, and making such determinations is within the skill in the art Inhibition includes both reduction and elimination of β-lactamase activity.

The present compounds, and the pharmaceutically-acceptable salts thereof, can be used to treat β-lactam-antibiotic-resistant bacterial infections. "β-lactam-antibiotic-resistant bacterial infection" is used herein to refer to an infection caused by bacteria resistant to treatment with one or more B-lactam antibiotics due primarily to the action of a β-lactamase. Resistance to B-lactam antibiotics can be determined by standard antibiotic sensitivity testing. The presence of β-lactamase activity can be determined as is well known in the art (see above). Alternatively, the sensitivity of a particular bacterium to the combination of an inventive compound, or a pharmaceutically-acceptable salt thereof, and a β-lactam antibiotic can be determined by standard antibiotic sensitivity testing methods.

To treat a β-lactam resistant bacterial infection, an animal or subject suffering from such an infection is given an effective amount of a compound of this invention, or a pharmaceutically-acceptable salt thereof, and an effective amount of a β-lactam antibiotic. Such a compound, or a pharmaceutically-acceptable salt thereof, and the β-lactam antibiotic may be given at different times or given together. When administered together, they may be contained in separate pharmaceutical compositions or they may be in the same pharmaceutical composition.

Many suitable β-lactam antibiotics are known in the art, including but not limited to the cephalosporins, penicillins, monobactams, carbapenems, and carbacephems. β-lactam antibiotics are effective (in the absence of resistance) against a wide range of bacterial infections. These include those caused by both gram-positive and gram-negative bacteria, for example, bacteria of the genus *Staphylococcus* (such as *Staphylococcus aureus* and *Staphylococcus epidermidis*), *Streptococcus* (such as *Streptococcus agalactine, Streptococcus penumoniae* and *Streptococcus faecalis*), *Micrococcus* (such as *Micrococcus luteus*), *Bacillus* (such as *Bacillus subtilis*), *Listerella* (such as Listerella monocytogenes), *Escherichia* (such as *Escherichia coli*), *Klebsiella* (such as *Klebsiella pneumoniae*), *Proteus* (such as *Proteus mirabilis* and *Proteus vulgaris*), *Salmonella* (such as *Salmonella typhosa*), *Shigella* (such as *Shigella sonnei*), *Enterobacter* (such as *Enterobacter aerogenes* and *Enterobacter Cloacae*), *Serratia* (such as *Serratia marcescens*), *Pseudomonas* (such as *Pseudomonas aeruginosa*), *Acinetobacter* (such as *Acinetobacter anitratus*), *Nocardia* (such as *Nocardia autotrophica*), and *Mycobacterium* (such as *Mycobacterium fortuitum*). Effective doses and modes of administration of β-lactam antibiotics are known in the art or may be determined empirically or as described below for such compounds.

To treat an animal/subject suffering from a β-lactam-antibiotic-resistant bacterial infection, an effective amount of one or more of the present compounds, or a pharmaceutically-acceptable salt thereof, is administered in combination with a β-lactam antibiotic. Effective dosage forms, modes of administration and dosage amounts may be determined empirically, and making such determinations is within the skill of the art. It is understood by those skilled in the art that the dosage amount will vary with the activity of the particular compound employed, the severity of the bacterial infection, the route of administration, the rate of excretion of the compound, the duration of the treatment, the identity of any other drugs being administered to the animal/subject, the age, size and species of the animal, and like factors well known in the medical and veterinary arts. In general, a suitable daily dose will be that amount which is the lowest dose effective to produce a therapeutic effect. The total daily dosage will be determined by an attending physician or veterinarian within the scope of sound medical judgment. If desired, the effective daily dose of such a compound, or a pharmaceutically-acceptable salt thereof, maybe administered as two, three, four, five, six or more sub-doses, administered separately at appropriate intervals throughout the day. Treatment of a β-lactam-antibiotic-resistant bacterial infection according to the invention, includes mitigation, as well as elimination, of the infection. Animals treatable according to the invention include mammals. Mammals treatable according to the invention include, dogs, cats, other domestic animals, and humans.

Compounds of this invention may be administered to an animal/patient for therapy by any suitable route of administration, including orally, nasally, rectally, intravaginally, parenterally, intracisternally and topically, as by powders, ointments or drops, including buccally and sublingually. The preferred routes of administration are orally and parenterally.

While it is possible for the active ingredient(s) (one or more compounds of this invention and/or pharmaceutically-acceptable salts thereof, alone or in combination with a β-lactam antibiotic) to be administered alone, it is preferable to administer the active ingredient(s) as a pharmaceutical formulation (composition). The pharmaceutical compositions of the invention comprise the active ingredient(s) in admixture with one or more pharmaceutically-acceptable carriers and, optionally, with one or more other compounds, drugs or other materials. Each carrier must be "acceptable" in the sense of being compatible with the other ingredients of the formulation and not injurious to the patient.

Pharmaceutical formulations of the present invention include those suitable for oral, nasal, topical (including buccal and sublingual), rectal, vaginal and/or parenteral administration. Regardless of the route of administration selected, the active ingredient(s) are formulated into pharmaceutically-acceptable dosage forms by conventional methods known to those of skill in the art.

The amount of the active ingredient(s) which will be combined with a carrier material to produce a single dosage form will vary depending upon the host being treated, the particular mode of administration and all of the other factors described above. The amount of the active ingredient(s) which will be combined with a carrier material to produce a single dosage form will generally be that amount of the active ingredient(s) which is the lowest dose effective to produce a therapeutic effect.

Methods of preparing pharmaceutical formulations or compositions include the step of bringing the active ingredient(s) into association with the carrier and, optionally, one or more accessory ingredients. In general, the formulations are prepared by uniformly and intimately bringing the active ingredient(s) into association with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or nonaqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of the active ingredient(s). The active ingredient(s) may also be administered as a bolus, electuary or paste.

In solid dosage forms of the invention for oral administration (capsules, tablets, pills, dragees, powders, granules and the like), the active ingredient(s) is/are mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethyl-cellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient(s) moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient(s) therein using, for example, hydroxypropylmethyl cellulose in varying proportions to provide the desired release profile, other polymer matrices, liposomes and/or microspheres. They may be sterilized by, for example, filtration through a bacteria-retaining filter. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient(s) can also be in microencapsulated form.

Liquid dosage forms for oral administration of the active ingredient(s) include pharmaceutically-acceptable emulsions, microemulsions, solutions, suspensions, syrups and elixirs. In addition to the active ingredient(s), the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents. Suspensions, in addition to the active ingredient(s), may contain suspending agents as, for example, ethoxylated isostearyl alcohols, polyoxyethylene sorbitol and sorbitan esters, microcrystalline cellulose, aluminum metahydroxide, bentonite, agar and tragacanth, and mixtures thereof.

Formulations of the pharmaceutical compositions of the invention for rectal or vaginal administration may be presented as a suppository, which may be prepared by mixing the active ingredient(s) with one or more suitable nonirritating excipients or carriers comprising, for example, cocoa butter, polyethylene glycol, a suppository wax or salicylate and which is solid at room temperature, but liquid at body temperature and, therefore, will melt in the rectum or vaginal cavity and release the active ingredient(s). Formulations of the present invention which are suitable for vaginal administration also include pessaries, tampons, creams, gels, pastes, foams or spray formulations containing such carriers as are known in the art to be appropriate.

Dosage forms for the topical or transdermal administration of the active ingredient(s) include powders, sprays, ointments, pastes, creams, lotions, gels, solutions, patches and inhalants. The active ingredient(s) may be mixed under sterile conditions with a pharmaceutically-acceptable carrier, and with any buffers, or propellants which may be required.

The ointments, pastes, creams and gels may contain, in addition to the active ingredient(s), excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to the active ingredient(s), excipients such as lactose, talc, silicic acid, aluminum hydroxide, calcium silicates and polyamide powder, or mixtures of these substances. Sprays can additionally contain customary propellants such as chlorofluorohydrocarbons and volatile unsubstituted hydrocarbons, such as butane and propane.

Transdermal patches have the added advantage of providing controlled delivery of the active ingredient(s) to the body. Such dosage forms can be made by dissolving, dispersing or otherwise incorporating the active ingredient(s) in a proper medium, such as an elastomeric matrix material. Absorption enhancers can also be used to increase the flux of the active ingredient(s) across the skin. The rate of such flux can be controlled by either providing a rate-controlling membrane or dispersing the active ingredient(s) in a polymer matrix or gel.

Pharmaceutical compositions of this invention suitable for parenteral administration comprise the active ingredient(s) in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monostearate and gelatin.

In some cases, in order to prolong the effect of the active ingredient(s), it is desirable to slow the absorption of the drug from subcutaneous or intramuscular injection. This may be accomplished by the use of a liquid suspension of crystalline or amorphous material having poor water solubility. The rate of absorption of the active ingredient(s) then depends upon its/their rate of dissolution which, in turn, may depend upon crystal size and crystalline form. Alternatively, delayed absorption of parenterally-administered active ingredient(s) is accomplished by dissolving or suspending the active ingredient(s) in an oil vehicle.

Injectable depot forms are made by forming microencapsule matrices of the active ingredient(s) in biodegradable polymers such as polylactide-polyglycolide. Depending on the ratio of the active ingredient(s) to polymer, and the nature of the particular polymer employed, the rate of release of the active ingredient(s) can be controlled. Examples of other biodegradable polymers include poly(orthoesters) and poly (anhydrides). Depot injectable formulations are also prepared by entrapping the active ingredient(s) in liposomes or microemulsions which are compatible with body tissue. The injectable materials can be sterilized, for example, by filtration through a bacterial-retaining filter.

The formulations may be presented in unit-dose or multi-dose sealed containers, for example, ampoules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above. The pharmaceutical compositions of the present invention may also be used in the form of veterinary formulations, including those adapted for the following: (1) oral administration, for example, drenches (aqueous or nonaqueous solutions or suspensions), tablets, boluses, powders, granules or pellets for admixture with feed stuffs, pastes for application to the tongue; (2) parenteral administration, for example, by subcutaneous, intramuscular or intravenous injection as, for example, a sterile solution or suspension or, when appropriate, by intramammary injection where a suspension or solution is introduced into the udder of the animal via its teat; (3) topical application, for example, as a cream, ointment or spray applied to the skin; or (4) intravaginally, for example, as a pessary, cream or foam.

EXAMPLES OF THE INVENTION

Materials and Methods

Synthesis and analysis. All reactions were performed under argon using oven-dried glassware. Solvents were dried according to classical procedures. A cold bath at $-100°$ C. was prepared by addition of liquid nitrogen to a pre-cooled ($-80°$ C.) mixture of 1:1 EtOH/MeOH. Chromatographic purification of the compounds was performed on silica gel (0.05-0.20 mm) Melting points were obtained on a Büchi 510 apparatus and are uncorrected. Optical rotations were recorded at 20° C. on a Perkin-Elmer 241 polarimeter and are in $10^{-1}$ deg $cm^2$ $g^{-1}$. IR spectra were determined in KBr pellets (for solids) and films (for liquids) on a Perkin Elmer 1600 Series spectrophotometer. $^1$H and $^{13}$C-NMR spectra were recorded on a Bruker DPX-200 (at 200 and 50 MHz, respectively) spectrometer: chemical shifts are reported in δ values from TMS as the internal standard. Mass spectra were determined on a Finnigan MAT SSQ A mass spectrometer (EI, 70 eV). Elemental analyses were performed on a Carlo Erba Elemental Analyzer 1110. 2-(3-bromophenyl)-4,4-dimethyl-4,5-dihydro-oxazole (6) was synthesized as described.

Example 1

(+)-pinanediol 3-(4,4-dimethyl-4,5-dihydro-oxazol-2-yl) phenylboronate (7). n-BuLi (2.5 mL of a 2.5 M solution in hexane, 6.23 mmol) was added dropwise with stirring to a solution of 6 (1.51 g, 5.93 mmol) in THF (9.5 mL) at $-78°$ C. under argon. After 30 min a solution of trimethylborate (0.7 mL, 5.93 mmol) in THF (2 mL) was added and the mixture stirred for 1.5 h; thereafter, the resulting yellow solution was quenched with TMSCl (0.75 mL, 5.93 mmol) and allowed to reach rt. After 1 h (+)-pinanediol (1.01 g, 5.93 mmol) dissolved in a minimum amount of anhydrous $Et_2O$ was added one portion to the solution, and then stirred overnight. The reaction mixture was partitioned in $Et_2O$ (16 mL) and $H_2O$ (10 mL) and the aqueous phase extracted with $Et_2O$ (2×10 mL). The combined organic phases were dried on $MgSO_4$, filtered and concentrated to give an orange oil, which was purified by chromatography (7:3 EtPet/EtOAc) and crystallization (EtPet), affording 7 (1.14 g, 54%) as a white crystalline solid, mp 98-101° C., $[\alpha]_D$=+11.2 (c 1.5, $CHCl_3$). IR (KBr): 1646 cm$^{-1}$. $^1$H NMR ($CDCl_3$): δ 0.81 (3H, s, pinanyl $CH_3$), 1.22 (1H, d, J=10.5 Hz, pinanyl $H_{endo}$), 1.33 (3H, s, pinanyl $CH_3$), 1.40 (6H, s, $2CH_3$), 1.50 (3H, s, pinanyl $CH_3$), 1.5-2.5 (5H, m, pinanyl protons), 4.22 (2H, s, $CH_2O$), 4.47 (1H, dd, J=8.8, 2.0 Hz, pinanyl CHOB), 7.43 (1H, t, J=7.7 Hz, $H_5$ arom.), 7.92 (1H, dt, J=7.7, 1.5 Hz, $H_6$ arom.), 8.05 (1H, dt, J=7.7, 1.5 Hz, $H_4$ arom.), 8.43 (1H, br s, $H_2$ arom.). $^{13}$C NMR ($CDCl_3$): δ24.4, 26.9, 27.5, 28.8 (2C), 29.1, 35.9, 38.6, 40.0, 51.9, 68.0, 78.8, 79.5, 86.8, 128.1, 131.2, 135.0, 137.8, 162.5, (CB and aromatic quaternary C not seen). EI-MS: m/z 353 ($M^+$), 338 (base peak), 323, 282, 242, 202, 186, 130, 103, 67, 55. Anal. Calcd for $C_{21}H_{28}NO_3B$: C, 71.39; H, 7.99; N 3.96. Found: C, 71.01; H, 8.65; N, 3.89.

Example 2

One pot general procedure for the synthesis of (+)-pinanediol (1R)-1-acylamino-1-[3-(4,4-dimethyl-4,5-dihydro-oxazol-2-yl)phenyl]methylboronate (10-12). Dichloromethyllithium was generated by adding n-BuLi (1.24 mL of a 2.5 M solution in hexane, 3.11 mmol) dropwise to a solution of $CH_2Cl_2$ (0.29 mL, 4.53 mmol) in THF (10 mL) with stirring at −100° C. under argon: toward the end of the BuLi addition, precipitation of the white microcrystalline $LiCHCl_2$ became evident. After 30 min the mixture was treated with the above pinanediol boronate 7 (1.00 g, 2.83 mmol) and allowed to reach rt with stirring. The tetrahedral boronate adduct precipitated as an abundant white solid at −80° C., and redissolved upon warming. After 1 h at 0° C. the solution was cooled to −78° C.; $LiN(TMS)_2$ (3.11 mL of a 1 M solution in THF, 3.11 mmol) was added and the resulting solution allowed to warm gradually to 20° C. and stirred overnight. The desilylation, acylation, and purification of the product were carried out as described for compounds 10-12.

Example 3

Analytical sample of compounds 8 and 9 were prepared and characterized.

(+)-pinanediol(1S)-1-chloro-1-[3-(4,4-dimethyl-4,5-dihydro-oxazol-2-yl)phenyl]methylboronate (8): $[\alpha]_D$=+3.5 (c 2.3, $CHCl_3$). IR (film): 1650 cm$^{-1}$. $^1$H NMR ($CDCl_3$): 0.86 (3H, s, pinanyl $CH_3$), 1.17 (1H, d, J=10.5, pinanyl $H_{endo}$), 1.31 (3H, s, pinanyl $CH_3$), 1.41 (6H, s, $2CH_3$), 1.43 (3H, s, pinanyl $CH_3$), 1.5-2.5 (5H, m, pinanyl protons), 4.13 (2H, s, $CH_2O$), 4.41 (1H, dd, J=8.8, 2.0, pinanyl CHOB), 4.58 (1H, br s, CHB), 7.41 (1H, t, J=7.7, $H_5$ arom.), 7.64 (1H, dt, J=7.7, 1.5, $H_6$ arom.), 7.88 (1H, dt, J=7.7, 1.5, $H_4$ arom.), 8.02 (1H, t, J=1.5, $H_2$ arom.). $^{13}$C NMR ($CDCl_3$): δ24.3, 26.6, 27.4, 28.7 (3C), 35.6, 38.6, 39.7, 45.0 (br, CB), 51.7, 67.7, 79.3, 79.6, 87.5, 128.1, 128.6, 129.0, 131.7, 139.6, 162.2. EI-MS: m/z 401-403 ($M^+$), 386-388, 371-373, 250-252, 223-225 (base peak), 189, 135, 93, 67, 55.

(+)-pinanediol (1R)-1-(N-bistrimethylsilylamino)-1-[3-(4,4-dimethyl-4,5-dihydro-oxazol-2-yl)phenyl]methyboronate (9). $[\alpha]_D$=−2.7 (c 2.0, $CHCl_3$). IR (film): 1650 cm$^{-1}$. $^1$H NMR ($CDCl_3$): δ0.13 (18H, $2Si(CH_3)_3$), 0.89 (3H, s, pinanyl $CH_3$), 1.30 (1H, d, J=10.5, pinanyl $H_{endo}$), 1.35 (3H, s, pinanyl $CH_3$), 1.41 (6H, s, $2CH_3$), 1.46 (3H, s, pinanyl $CH_3$), 1.5-2.5 (5H, m, pinanyl protons), 4.12 (2H, s, $CH_2O$), 4.14 (1H, br s, CHB), 4.39 (1H, dd, J=8.8, 2.0, pinanyl CHOB), 7.33 (1H, t, J=7.7, $H_5$ arom.), 7.62 (1H, dm, J=7.7, $H_4$ arom.), 7.79 (1H, dm, J=7.7, $H_6$ arom.), 8.05 (1H, m, $H_2$ arom.). $^{13}$C NMR ($CDCl_3$): δ2.8 (6C), 24.4, 26.9, 27.4, 28.7 (3C), 35.8, 38.6, 39.9, 47.0 (br, CB), 51.9, 67.8, 79.0, 79.4, 86.5, 125.8, 127.1, 127.6, 127.9, 129.7, 145.587, 163.1. ELMS: m/z 526 ($M^+$), 511, 453, 275, 203, 135, 130, 93, 73 (base peak), 67, 55.

Example 4

(+)-pinanediol (1R)-1-acetylamino-1-[3-(4,4-dimethyl-4,5-dihydro-oxazol-2-yl)phenyl]methylboronate (10). After 16 h at rt the reaction mixture containing the silylamino derivative 9 was cooled at −78° C. and treated with a solution of $Ac_2O$ (1.13 mL, 12.00 mmol) and AcOH (194 µl, 3.40 mmol) in THF (2 mL), then allowed to warm to rt and stirred overnight. The solution was partitioned in EtOAc (60 mL) and $H_2O$ (12 mL) and the aqueous phase was extracted with EtOAc (2×15 mL). The combined organic phases were washed with 5% $NaHCO_3$, $H_2O$ (6.5 mL), and saturated NaCl (6.5 mL), dried ($MgSO_4$) and concentrated in vacuo to give a brownish oil which was purified by chromatography (95:5 $Et_2O$/MeOH) and crystallization (EtOAc), affording 10 (291 mg, 24% overall yield from 7) as a white solid, mp 196° C., $[\alpha]_D$=−136.9 (c 2.1, $CHCl_3$), de>98%. IR (KBr): 1648, 1600 cm$^{-1}$. $^1$H NMR ($CDCl_3$): δ 0.80 (3H, s, pinanyl $CH_3$), 1.22 (9H, br s, $2CH_3$-pinanyl $CH_3$), 1.32 (3H, s, pinanyl $CH_3$), 1.39 (1H, d, J=10.5 Hz, pinanyl $H_{endo}$), 1.5-2.5 (8H, m, pinanyl protons and $CH_3CONH$ at 2.16, d, J=0.67 Hz), 3.92 (1H, br s, CHB), 4.05 (3H, m, pinanyl CHOB—$CH_2O$), 7.28 (2H, m, $H_5$-$H_6$ arom.), 7.68 (2H, m, $H_2$—$H_4$ arom.), 10.18 (1H, br, NHCO). $^{13}$C NMR ($CDCl_3$): δ 18.1, 24.5, 27.0, 27.8, 28.5, 28.7, 29.5, 37.1, 38.5, 40.5, 51.0 (br, CB), 53.0, 67.7, 76.6, 79.4, 83.4, 125.0, 125.8, 127.7, 128.4, 130.3, 142.7, 163.363, 177.0. EI-MS: m/z 424 ($M^+$), 381, 272, 245 (base peak), 228, 203, 131, 93, 67, 55. Anal. Calcd for $C_{24}H_{33}BN_2O_4$: C, 67.90; H, 7.84; N, 6.60. Found: C, 68.32; H, 7.59; N, 6.31.

Example 5

(+) pinanediol (1R)-1-(2-thienylacetylamino)-1-[3-(4,4-dimethyl-4,5-dihydro-oxazol-2-yl)phenyl]methylboronate (11). Anhydrous MeOH (1.24 mL of a 2.5 M solution in THF, 3.11 mmol) was added to the solution containing the silylamino derivative 9 and stirred for 1 h at −10° C. and then for 1 h at rt. The solution was cooled at −78° C., 2-thiophenacetylchloride (383 µl, 3.11 mmol) in THF (1 mL) was slowly added and the resulting mixture was allowed to warm to rt overnight. EtOAc (65 mL) and $H_2O$ (15 mL) were added and the aqueous phase was extracted with EtOAc (2×15 mL). The combined organic phases were dried (MgSO4) and concentrated to give an orange oil which was purified by gradient chromatography (9:1 EtOAc/EtPet, 95:5 EtOAc/MeOH), affording 11 (360 mg, 25% overall yield from 7) as a pale orange solid, mp 120° C., $[\alpha]_D$=−24.2 (c 2.1, $CDCl_3$), de>98%. IR (KBr): 1646, 1600 cm$^{-1}$. $^1$H NMR ($CDCl_3$): δ 0.84 (3H, s, pinanyl $CH_3$), 1.23 (1H, d, J=10.5 Hz, pinanyl $H_{endo}$.), 1.27 (1H, s, pinanyl $CH_3$), 1.37 (3H, s, pinanyl $CH_3$), 1.38 (3H, s, $CH_3$), 1.39 (3H, s, $CH_3$), 1.5-2.5 (5H, m, pinanyl protons), 4.13 (1H, br d, J=2.0 Hz, CHB), 4.01 (2H, br s, $CH_2CONH$), 4.11 (2H, s, $CH_2O$), 4.25 (1H, dd, J=8.8, 2.0 Hz, pinanyl CHOB), 6.86 (1H, br, NHCO), 7.01 (2H, m, CHCHS—CHCS), 7.33 (3H, m, CHCHS—$H_6$—$H_5$ arom.), 7.77 (2H, m, $H_2$—$H_4$ arom.). $^{13}$C NMR ($CDCl_3$): δ 24.8, 27.2, 28.0, 28.58, 28.64, 29.5, 34.3, 36.9, 38.8, 40.6, 48.4 (br, CB), 52.9, 67.2, 77.7, 80.7, 84.8, 125.5, 126.7, 126.9, 128.0, 128.7, 129.1, 132.0, 134.6, 142.4, 175.5, (two quaternary C not seen). EI-MS: m/z 506 ($M^+$, base peak), 473, 327, 270, 203, 135, 97, 93, 67, 55. Anal. Calcd for $C_{28}H_{35}BN_2O_4S$: C, 66.40; H, 6.97; N, 5.53; S 6.33. Found: C, 66.26; H, 7.23; N, 5.29; S 6.58.

Example 6

(+)-pinanediol (1R)-1-{[3-(2-Chlorophenyl)-5-methyl-isoxazole-4-carbonyl]-amino}-1-[3-(4,4-dimethyl-4,5-dihydro-oxazol-2-yl)phenyl]methylboronate (12). The boronate 12 was prepared on the same scale following the procedure described for 11 using 3-(2-chlorophenyl)-5-methylisoxazolyl-4-carbonylchloride (796 mg, 3.11 mmol) as the acylating agent. After extraction, the combined organic phases were dried (MgSO$_4$) and concentrated in vacuo to give an orange oil which was purified by gradient chromatography (Et$_2$O, 95:5 Et$_2$O/MeOH) and triturated with Et$_2$O, affording 12 (276 mg, 16% overall yield from 7) as a pale yellow solid, mp 140° C., $[\alpha]_D$=+182.7 (c 2.0, CHCl$_3$), de>98%. IR (KBr): 1647, 1601 cm$^{-1}$. $^1$H NMR (CDCl$_3$): δ0.83 (3H, s, pinanyl CH$_3$), 1.10 (1H, d, J=10.5 Hz, pinanyl H$_{endo}$), 1.28 (3H, s, pinanyl CH$_3$), 1.33 (3H, s, pinanyl CH$_3$), 1.41 (6H, s, 2CH$_3$), 1.5-2.5 (5H, m, pinanyl protons), 2.84 (3H, s, CH$_3$CON), 4.12 (2H, s, CH$_2$O), 4.19 (1H, dd, J=8.8, 2.0 Hz, pinanyl CHOB), 4.22 (1H, br d, J=2.4 Hz, CHB), 6.10 (1H, br d, J=2.4 Hz, NHCO), 7.19 (1H, dt, J=7.5, 1.6 Hz, H$_4$ arom.), 7.30 (1H, t, J=7.5 Hz, H$_5$ arom.), 7.51 (4H, m, other aromatic protons), 7.67 (1H, m, J=1.6 Hz, H$_2$ arom.), 7.78 (1H, dt, J=7.5, 1.6 Hz, H$_6$ arom.). $^{13}$C NMR (CDCl$_3$): δ 13.8, 24.4, 26.7, 27.8, 28.8 (2C), 29.0, 36.2, 38.5, 40.0, 45.2 (br, CB), 52.2, 67.9, 78.0, 79.5, 85.6, 126.3, 126.7, 128.0, 128.7, 129.6, 130.9, 131.9, 132.4, 134.4, 140.7, 163.7, 176.2, (isoxazole quaternary C not seen). EI-MS: m/z 601-603 (M$^+$), 566 (base peak), 449, 423-425, 338, 316, 203, 178, 131, 93, 67, 55. Anal. Calcd for $C_{33}H_{37}BN_3O_5Cl$: C, 65.85; H, 6.20; N, 6.98. Found: C, 65.59; H, 6.28; N, 6.83.

Example 7a

General procedure for the synthesis of free boronic acids 15-17. The pinanediol esters 10-12 (0.30 mmol) were deprotected in degassed HCl (3 N, 7 mL) for 1 h at 120° C. under argon, and the resulting mixture was extracted with EtOAc (2×15 mL). The corresponding hydrolysis products 15 and 16 were isolated from the aqueous phase, while compound 17 was isolated from the organic phase.

Example 7b (1R)-1-acetylamino-1-(3-carboxyphenyl)methylboronic acid (15). The free boronic acid 15 was isolated from the aqueous phase after removal of the solvent under reduced pressure. Crystallization of the crude residue (boiling acetone) afforded 15 together with an equimolar amount of 2-methyl-2-amino-1-propanol as a light brown solid (58 mg, 59%), mp 90-92° C. IR (KBr): 3425, 1698, 1620 cm$^{-1}$. $^1$H NMR (DMSO): δ1.20 (6H, s, 2CH$_3$), 2.10 (4H, br s, CH$_3$CONH—CHB), 3.35 (2H, s, CH$_2$O), 6.98 (1H, d, J=7.8 Hz, H$_6$ arom.), 7.28 (1H, t, J=7.8 Hz, H$_5$ arom.), 7.56 (1H, s, H$_2$ arom.), 7.69 (1H, d, J=7.8 Hz, H$_4$ arom.), 8.02 (3H, br, B(OH)$_2$—COOH), 9.42 (1H, br, NHCO). $^{13}$C NMR (DMSO): δ 18.5, 23.1 (2C), 31 (br, CB), 55.3, 37.3, 126.5, 126.7, 128.3, 130.9, 143.7, 168.5, 176.0. The ELMS was not obtainable.

Example 7c (1R)-1-(2-thienylacetylamino)-1-(3-carboxyphenyl)methylboronic acid (16). The free boronic acid 16 was isolated from the aqueous phase after removal of the solvent under reduced pressure. Crystallization of the crude residue (H$_2$O) afforded 16 as an ivory solid (51 mg, 55%), mp 228° C. (dec), $[\alpha]_D$=−65.5 (c 0.5, CH$_3$OH). IR (KBr): 3398, 1704, 1606 cm$^{-1}$. $^1$H NMR (CD$_3$OD): δ 3.98 (1H, br s, CHB), 4.27 (2H, s, CH$_2$CONH), 7.05 (1H, dd, J=5.1, 3.2 Hz, CHCHS), 7.19 (1H, br d, J=3.2 Hz, CHCS), 7.41 (3H, m, CHCHS and H$_5$—H$_6$ arom.), 7.85 (2H, m, H$_2$—H$_4$ arom.). $^{13}$C NMR (CD$_3$OD): δ31.0, 53.0 (br, CB), 55.3, 126.2, 127.0, 127.2, 127.4, 128.2, 128.4, 130.6, 130.8, 133.5, 141.5, 168.9, 178.5. Anal. Calcd for $C_{14}H_{14}BNO_5S$: C, 52.69; H, 4.42; N, 4.39; S 10.05. Found: C, 52.71; H, 4.59; N, 4.31; S 9.87. The ELMS was not obtainable.

Example 7d (1R)-1-{[3-(2-Chlorophenyl)-5-methyl-isoxazole-4-carbonyl]-amino}-1-(3-carboxyphenyl)methylboronic acid (17). The free boronic acid 17 was obtained from the organic phase after anhydrification (MgSO$_4$). Removal of the solvent under reduced pressure and crystallization of the crude residue (acetone/Et$_2$O) afforded an ivory solid (82 mg, 50%), mp 180-190° C., $[\alpha]_D$=−36.3 (c 0.3, CH$_3$OH). IR (KBr): 3409, 1702, 1630 cm$^{-1}$. $^1$H NMR (DMSO): δ2.65 (3H, s, CH$_3$CON), 3.58 (1H, br s, CHB), 6.90 (1H, d, J=7.2 Hz, H$_6$ arom.), 7.11 (1H, t, J=7.2 Hz, H$_5$ arom.), 7.50 (8H, m, other aromatic protons-B(OH)$_2$), 8.9 (0.5H, br, NHCO), 12.6 (1H, br, COON). $^{13}$C NMR (DMSO): δ 12.5, 51.0 (br, CB), 125.7, 126.2, 126.7, 127.3, 127.4, 129.7, 129.8, 130.4, 131.5, 131.6, 131.7, 132.6, 142.6, 159.2, 163.8, 167.5, 172.8. Anal. Calcd for $C_{19}H_{16}BClN_2O_6$: C, 55.04; H, 3.89; N, 6.76. Found: C, 54.91; H, 4.03; N, 6.51. The ELMS was not obtainable.

Example 8

(+)-pinanediolphenylboronate (19). A solution of (+)-pinanediol (665 mg, 3.9 mmol) and phenylboronic acid (18) (476 mg, 3.9 mmol) in THF (5 mL) was stirred for 10 min, concentrated and distilled to yield 21 (879 mg, 88%) by 135° C. (1.5 mmHg) as a viscous colorless oil which solidified on standing, mp 50° C., $[\ ]_D$=+14.9 (c 2.3, CHCl$_3$). IR (KBr): 2910, 1361, 1094, 701 cm$^{-1}$. $^1$H NMR (CDCl$_3$): δ0.92 (3H, s, pinanyl CH$_3$), 1.25 (1H, d, J=10.5 Hz, pinanyl H$_{endo}$), 1.34 (3H, s, pinanyl CH$_3$), 1.50 (3H, s, pinanyl CH$_3$), 1.9-2.6 (5H, m, pinanyl protons), 4.48 (1H, dd, J=8.8, 2.0 Hz, pinanyl CHOB), 7.34-7.54 (3H, m, H$_m$—H$_p$), 7.85 (2H, dd, J=7.9 Hz, 1.6, H$_o$). $^{13}$C NMR (CDCl$_3$): δ24.4, 26.9, 27.5, 29.1, 36.0, 38.6, 40.0, 51.9, 78.7, 86.6, 128.1, 131.5, 135.2. Aromatic CB not seen. EI-MS: m/z 256 (M$^+$), 241, 215, 187, 173, 108 (base peak), 93, 77. Anal. Calcd for $C_{16}H_{21}BO_2$: C, 75.02; H, 8.26. Found: C, 74.77; H, 8.53.

Example 9

(+) pinanediol (1R)-1-(2-thienylacetylamino)-1-phenylmethylboronate (20). The product was synthesized from 19 (700 mg, 2.73 mmol) following the procedure described for 11. The crude residue was purified by chromatography (7:3 EtPet/EtOAc), affording 20 as a white solid (631 mg, 56% overall yield), mp 50-55° C., $[\alpha]_D$=+7.1 (c 2.4, CHCl$_3$), de>98%. IR (KBr): 1602 cm$^{-1}$. $^1$H NMR (CDCl$_3$): δ0.80 (3H, s, pinanyl CH$_3$), 1.15 (1H, d, J=10.5 Hz, pinanyl H$_{endo}$), 1.23 (3H, s, pinanyl CH$_3$), 1.35 (3H, s, pinanyl CH$_3$), 1.4-2.5 (5H, m, pinanyl protons), 3.97 (2H, br s, CH$_2$CONH), 4.06 (2H, br s, CHB), 4.22 (2H, dd, J=8.8, 2.0 Hz, pinanyl CHOB), 6.53 (1H, br, NHCO), 7.00 (2H, m, CHCHS—H$_p$), 7.18 (3H, m H$_m$—CHS), 7.26 (3H, m CHCS—H$_o$). $^{13}$C NMR (CDCl$_3$):

δ24.8, 27.0, 27.9, 29.3, 35.2, 36.7, 38.8, 40.5, 47.5 (br, CB), 52.7, 78.0, 85.4, 126.8, 126.9, 127.0, 128.3, 128.8, 129.1, 135.3, 140.9, 174.3. EI-MS: m/z 409 (base peak, M+), 394, 376, 340, 311, 284, 257, 230, 173, 117, 97, 91, 69. Anal. Calcd for $C_{23}H_{28}BNO_3S$: C, 67.48; H, 6.89; N, 3.42; S 7.83. Found: C, 67.21; H, 7.01; N, 3.36; S 7.52.

Example 10

(1R)-1-(2-thienylacetylamino)-1-phenylmethylboronic acid (21). The product was synthesized from 20 (387 mg, 0.95 mmol) following the protocol described for 15-17. The aqueous phases was concentrated, affording the free boronic acid 21 as an ivory solid (103 mg, 58%.), mp 90-100° C., $[\alpha]_D$=−3.1 (c 2.1, $CD_3OD$). IR (KBr): 3420, 1628 cm⁻1. ¹H NMR ($CD_3OD$): δ3.82 (1H, br s, CHB), 4.16 (2H, br s, $CH_2CONH$), 6.98-7.32 (7H, m, CHCHS—CHCS—$H_o$—$H_m$—$H_p$), 7.38 (1H, dd, J=5.3, 1.0, CHCHS). ¹³C NMR ($CD_3OD$): δ30.9, 53.4 (br, CB), 125.7, 125.9, 126.0, 127.3, 128.0, 128.1, 129.0, 133.6, 178.0. Anal. Calcd for $C_{13}H_{14}BNO_3S$: C, 56.75; H, 5.13; N, 5.09; S 11.65. Found: C, 56.53; H, 5.07; N, 4.90; S 11.57. The ELMS was not obtainable.

Example 11

Enzymology. The phenylglycylboronic acids of the preceding examples were dissolved in DMSO at a concentration of 50 mM; more dilute stocks (10 mM to 1 µM) were subsequently prepared as necessary. Kinetic measurements were performed using nitrocefin as substrate in 50 mM Tris buffer, pH 7.0 and monitored in an HP8453 UV/Vis spectrophotometer. The concentration of AmpC was determined spectrophotometrically in stock solutions made from lyophilized powder; this enzyme had been previously expressed and purified. Usher, K. C., Blaszczak, L. C., Weston, G. S., Shoichet, B. K. and Remington, S. J. *Biochemistry* 1998, 37, 16082-16092. The concentration of enzyme in all reactions was 1.75 nM, except when assaying compound 16, where the concentration used was reduced two- to four-fold (the results from the 0.8 nM enzyme concentration reactions are reported here). To determine $K_i$ values, inhibitor and enzyme were incubated together at their final concentration in the cuvettes for five minutes before the reaction was initiated by the addition of 200 µM substrate. $K_i$ values for compounds 15, 16, 17, and 21 were obtained by comparison of progress curves in the presence and absence of inhibitor, using the method described by Waley, which has been widely used for boronic acid inhibitors of β-lactamases. Waley, S. G. *Biochem. J.* 1982, 205 631-633. In these analyses, sufficient inhibitor was used to give at least 50% inhibition; the Ki values reported are the average calculated from reactions at six different inhibitor concentrations, each of which was repeated three times. The lowest concentration of the 1 nM inhibitor 16 in these assays was 3 nM. Because this concentration approaches that of enzyme, inhibition values for these reactions were checked against reactions run with enzyme at 0.4 nM to ensure that the measured inhibition values were not significantly perturbed by the enzyme's effect on free inhibitor concentration. In all reactions, rates were measured after reactions had overcome their initial lag phase and had reached a steady state.

Example 12

Selectivity. The selectivity of compounds 16 and 21 was tested by determining their activity against the serine proteases α-chymotrypsin (bovine pancreatic), β-trypsin (bovine pancreatic), and elastase (porcine pancreatic), all from Sigma (St. Louis, Mo.). The substrates for α-chymotrypsin (succinyl-ala-ala-pro-phe-p-nitroanilide) and β-trypsin (N-benzoyl-L-arginine ethyl ester) were also purchased from Sigma. The elastase substrate (MeOSuc-Ala-Ala-Pro-Val-pNA) was purchased from Calbiochem (San Diego, Calif.). Substrates were diluted from 20 mM DMSO stock solutions, and all reactions were performed in 50 mM Tris buffer, pH 7.0, 25° C. For α-chymotrypsin, 0.001 mg/ml of enzyme and the inhibitor at its final concentration were incubated in the cuvette for five minutes before the reaction was initiated by the addition of 200 µM of substrate. The reaction was monitored at 410 nm. For β-trypsin, 0.004 mg/ml of enzyme and the inhibitor at its final concentration were incubated in the cuvette for five minutes before the reaction was initiated by the addition of 200 µM of substrate. The reaction was monitored at 253 nm. For elastase, 0.006 mg/ml of enzyme and the inhibitor at its final concentration were incubated in the cuvette for five minutes before the reaction was initiated by the addition of 640 µM of substrate. The reaction was monitored at 385 nm. Initial rate fits to the absorbance data for the first 100 seconds were used to determine reaction velocities.

Example 13

Crystal growth and structure determination. Co-crystals of AmpC in complex with compounds 16 and 21 were grown by vapor diffusion in hanging drops equilibrated over 1.7 M potassium phosphate buffer (pH 8.7) using micro-seeding techniques. The initial concentration of the protein in the drop was 3.8 mg/ml, and the concentration of compounds 16 and 21 were 705 µM and 588 µM, respectively. The compounds were added to the crystallization drops in a 1.2% DMSO, 1 M potassium phosphate buffer (pH 8.7) solution. Crystals appeared in 5-7 days after equilibration at 23° C. Before data collection, crystals were immersed in a cryoprotectant solution of 25% sucrose, 1.7 M potassium phosphate, pH 8.7, for about 30 seconds, and flash cooled in liquid nitrogen. Data were measured on DND-CAT beam line (51 DB) of the Advance Photon Source at Argonne National Lab at 100 K using a Mar-CCD detector. Both data sets were measured from single crystals. Reflections were indexed, integrated, and scaled using the HKL software package. For both structures the space group was C2, with two molecules in the asymmetric unit, each containing 358 residues. The initial phasing model was an AmpC/boronic acid complexed structure (PDB entry 1FSY), with inhibitor, water molecules, and ions removed. The model was positioned by rigid body refinement and refined using the maximum likelihood target in CNS including simulated annealing, positional minimization, and individual B-factor refinement, with a bulk solvent correction. Brunger, A. T., Adams, P. D., Clore, G. M., DeLano, W. L., Gros, P., Grosse-Kunstleve, R. W., Jiang, J. S., Kuszewski, J., Nilges, M., Pannu, N. S., Read, R. J., Rice, L. M., Simonson, T. and Warren, G. L. *Acta Crystallogr., Sect. D* 1998, 54, 905-921. Sigma A-weighted electron density maps were calculated using CNS and used in further steps of manual model rebuilding and placement of water molecules with the program O. The inhibitors were built into the 2|Fo|−|Fc| and |Fo|−|Fc| difference density maps in each active site of the asymmetric unit. Subsequent refinement cycles consisted of positional minimization and B-factor refinement in CNS.

Example 14

Microbiology. Compounds 16 and 21 were tested for synergy with the β-lactam ceftazidime against pathogenic bacteria from clinical isolates at the Hospital Ramón y Cajal; these bacteria were resistant to β-lactams due to expression of a class C β-lactamase. Strains of bacteria tested were: *Citrobacter freundii* mut756-CAZ, *Escherichia coli* 72929 Hip, *E. coli* 4774 Hip (Table 4, *E. coli* 1 and 2, respectively), *Enterobacter cloacae* 72527 ED, *E. cloacae* 8411 CAZ-R clon7, *E. cloacae* 12991 ED (Table 4, *E. cloacae* 1, 2, and 3, respectively), *Pseudomonas aeruginosa* 279/88, and *P. aeruginosa* JMSMA7 (Table 4, *P. aeruginosa* 1 and 2, respectively). Minimum inhibitor concentration (MIC) values were determined with Mueller-Hinton Broth II using the microdilution method according to NCCLS guidelines. National Committee for Clinical Laboratory Standards, Methods for dilution antimicrobial susceptibility test for bacteria that grow aerobically. Approved Standard M7-A4, 1997, vol. 17, National Committee for Clinical Laboratory Standards, Villanova, Pa.

Example 15

Data Deposition. The coordinates and structure factors have been deposited in the Protein Data Bank under accession codes 1MXO and 1MY8 for AmpC in complex with compound 16 and 21, respectively.

Example 16

Enzyme mutagenesis and preparation. Mutants of AmpC were created using the overlap extension polymerase chain reaction (23). Mutant enzymes were expressed as described. AmpC N289A and L293A were purified on an m-aminophenylboronic acid affinity column. AmpC L119A was purified on an S-Sepharose ion-exchange column. The purified enzymes were concentrated using Centricon spin concentrators.

Example 17

Mutant Enzymology. The glycylboronic acids were dissolved in DMSO at a concentration of 50 mM; more dilute stocks were subsequently prepared as necessary. Kinetic measurements were performed using nitrocefin as a substrate in 50 mM Tris buffer, pH 7.0, and monitored at 480 nm in an HP9453 UV-vis spectrophotometer. To prevent overestimation of inhibition due to sequestration of the enzyme on the walls of the cuvette during the reaction, 0.1% BSA was added to the buffer in all reactions. The $K_M$ values of nitrocefin for L119A, N289A, and L293A were 30804, 27 μM, and 33 μM respectively; the value for the wild-type enzyme is 127 μM. To determine $K_i$ values, inhibitor and enzyme were incubated together in the cuvettes for 5 min before reaction was initiated by the addition of substrate. 200 μM nitrocefin was used for the reactions with L119A and L293A, whereas 400 μM nitrocefin was used for the reactions with N289A to shorten the lag phase of the reaction. For the reactions with N289A, rates were calculated from the later portions of the curve, once the reactions had achieved steady state. These rates were compared with portions of the uninhibited curves that corresponded to the same range of substrate concentrations. $K_i$ values were calculated using the progress curve method described by Waley, which has been used extensively for boronic acid inhibitors of β-lactamase.

Example 18

Crystal Growth and Structure Determination. Cocrystals of AmpC N289A in complex with compounds 16 and 21 were grown by vapor diffusion in hanging drops equilibrated over 1.7 M potassium phosphate buffer (pH 8.7) using microseeding techniques (9, 14). The initial concentration of the protein in the drop was 3.8 mg/mL and the concentration of compounds 16 and 21 was 58804. The compounds were added to the drop in a 1.2% DMSO, 1 M potassium phosphate buffer (pH 8.7) solution.

Crystals appeared 5-7 days after equilibration at 23° C. Before data collection, crystals were immersed in a cryoprotectant solution of 23% sucrose, 1.7 M potassium phosphate, pH 8.7, for about 30 s, and were flash cooled in liquid nitrogen. Data were measured on the DND-CAT beam line (51 DB) of the Advanced Photon Source at Argonne National Laboratory at 100 K using a Mar-CCD detector. Both data sets were measured from single crystals. Reflections were indexed, integrated, and scaled using the HKL software package (25). For both structures the space group was C2, with two molecules in the asymmetric unit, each containing 358 residues. The initial phasing model for the 21/N289A structure was the 21/WT AmpC complexed structure (PDB code 1MY8) with the ligand and solvent removed. The 21/N289A structure without compound or solvent was then used as the initial phasing model for the 16/N289A structure. Initial rigid body refinement was followed by positional minimization and B-factor refinement, using CNS (26). Sigma A-weighted electron density maps were calculated in CNS and used for manual corrections of the protein model and water placement in TURBO (27). The boronic acid inhibitors were fitted into positive $F_o-F_c$ density. In the 16/N289A structure, the Asn→Ala substitution was visible as negative density in the $F_o-F_c$ density at position 289. Subsequent refinement cycles included compound and solvent and consisted of Cartesian and B-factor refinement in CNS. To create the wild-type/mutant crystal structure overlays (FIG. 11), the two structures were matched at the Cα of all 358 residues of the B monomers using MidasPlus. The RMS errors were 0.19 Å for the structures with compound 16 and 0.17 Å for the structures with compound 21.

Example 19

Data deposition. The coordinates and structure factors have been deposited in the Protein Data Bank under accession codes 1PI5 and 1PI4 for AmpC N289A in complex with compounds 16 and 21, respectively.

Example 20a

Synthesis and Analysis of Compound 26. Compound 26 was synthesized as outlined in Scheme 3. All reactions were performed under argon using oven-dried glassware. Solvents were dried according to classical procedures. A cold bath at −100° C. was prepared by addition of liquid nitrogen to a pre-cooled (−78° C.) mixture of 1:1 EtOH/MeOH. Chromatographic purification of the compounds was performed on silica gel (0.05-0.20 mm). Melting points were obtained on a Büchi 510 apparatus. Optical rotations were recorded at 20° C. on a Perkin-Elmer 241 polarimeter and are in $10^{-1}$ deg cm$^2$ g$^{-1}$. IR spectra were determined in KBr pellets (for solids) and films (for liquids) on a Perkin-Elmer 1600 Series spectrophotometer. $^1$H and $^{13}$C NMR spectra were recorded on a Bruker DPX-200 (at 200 and 50 MHz, respectively) spectrometer: chemical shifts are reported in δ values from TMS as the internal standard. Mass spectra were determined on a Finnigan MAT SSQ A mass spectrometer (EI, 70 eV). Elemental analyses were performed on a Carlo Erba Elemental Analyzer 1110.

Example 20b

1-Bromo-3-dimethoxymethyl-benzene (22b). Commercial 2-(3-Bromo-phenyl)-[1,3]dioxolane (1.3 mL, 8.64 mmol) was dissolved in anhydrous MeOH (40 mL) and catalytic amount of $H_2SO_4$ was added. The resulting reaction mixture was stirred 4 h at rt and finally extracted with petroleum ether (3×50 mL). The combined organic phases were washed with $NaHCO_3$ (40 mL), dried ($MgSO_4$), filtered and concentrated under vacuum to give 22b as a colourless oil (1.76 g, 88%), whose spectroscopic data were in close agreement with literature (29).

Example 20c (+)-Pinanediol (3-Dimethoxymethyl)phenylboronate (23b). n-BuLi (5.72 mL of a 2.5 M solution in hexane, 14.3 mmol) was added dropwise with stirring to a solution of 22b (3.00 g, 13.0 mmol) in THF (8 mL) at −78° C. under argon. After 30 min, a solution of trimethylborate (1.50 mL, 13.0 mmol) in THF (4 mL) was added, and the mixture was stirred for 1.5 h. The resulting turbid solution was quenched with TMSCl (1.65 mL, 13.0 mmol) and allowed to reach rt. After 4 h a clear yellow solution is obtained and (+)-pinanediol (2.21 g, 13.0 mmol) dissolved in a minimum amount of anhydrous $Et_2O$ was added and stirred overnight. The reaction mixture was partitioned in $Et_2O$ (75 mL) and $H_2O$ (25 mL), and the aqueous phase was extracted with $Et_2O$ (3×25 mL). The combined organic phases were dried on $MgSO_4$, filtered, and concentrated to give an orange oil, which was purified by gradient chromatography (9:1 to 7:3 EtPet/EtOAc), affording 23b (3.21 g, 75%) as a yellow liquid, $[\alpha]_D$=+7.80 (c 2.78, $CHCl_3$). $^1H$ NMR ($CDCl_3$): δ 0.88 (3H, s, pinanyl $CH_3$), 1.22 (1H, d, J=10.5 Hz, pinanyl $H_{endo}$), 1.30 (3H, s, pinanyl $CH_3$), 1.47 (3H, s, pinanyl $CH_3$), 1.8-2.6 (5H, m, pinanyl protons), 3.33 (6H, s, $CH(OCH_3)_2$), 4.44 (1H, dd, J=8.8, 1.8 Hz, pinanyl CHOB), 5.40 (1H, s, $CH(OCH_3)_2$), 7.37 (1H, t, J=7.6 Hz, $H_5$ Ph), 7.55 (1H, d, J=7.6 Hz, $H_6$ Ph), 7.78 (1H, d, J=7.6 Hz, $H_4$ Ph), 7.90 (1H, s, $H_2$ Ph). $^{13}C$ NMR ($CDCl_3$): δ 25.4, 27.9, 28.5, 30.1, 36.9, 39.6, 40.9, 52.8, 54.1, 79.7, 87.6, 104.7, 129.0, 130.8, 134.5, 136.3, 138.8 (CB and aromatic quaternary C not seen). EIMS: m/z 330 ($M^+$), 315, 299 (base peak), 289, 261, 247, 203, 147, 121, 105, 93, 91, 83, 75, 67.

Example 20d

Following the same procedure, starting from 22a, 23a was obtained together with variable quantities of 23b (5-50%). A careful gradient chromatography (9:1 to 1:1 EtPet/EtOAc) afforded an analitically pure sample of 23a as a colourless oil that solidifies on standing, mp 47° C., $[\alpha]_D$=+8.01 (c 2.12, $CHCl_3$). $^1H$ NMR ($CDCl_3$): δ 0.88 (3H, s, pinanyl $CH_3$), 1.22 (1H, d, J=10.5 Hz, pinanyl $H_{endo}$), 1.31 (3H, s, pinanyl $CH_3$), 1.47 (3H, s, pinanyl $CH_3$), 1.7-2.5 (5H, m, pinanyl protons), 4.05 (4H, m, $OCH_2CH_2O$), 4.44 (1H, dd, J=8.8, 1.8 Hz, pinanyl CHOB), 5.56 (1H, s, $PhCHOCH_2$), 7.39 (1H, t, J=7.7 Hz, $H_5$ Ph), 7.58 (1H, dt, J=7.7, 1.4 Hz, $H_6$ Ph), 7.83 (1H, dt, J=7.7, 1.4 Hz, $H_4$ Ph), 7.94 (1H, s, $H_2$ Ph). $^{13}C$ NMR ($CDCl_3$): δ 25.4, 27.9, 28.5, 30.1, 36.9, 39.5, 40.9, 52.8, 66.7, 66.6, 79.7, 87.6, 105.2, 129.1, 130.6, 134.3, 137.0, 138.7 (CB not seen). EIMS: m/z 328 ($M^+$), 327, 312, 259, 232, 231, 215, 187, 149 (base peak), 105, 77, 73, 51.

Example 21a

General Procedure for the Synthesis of (+)-Pinanediol (1R)-1-Acylamino-1-(3-formylphenyl)methylboronate (25, 26). Dichloromethyllithium was generated by adding n-BuLi (1.82 mL of a 2.5 M solution in hexane, 4.6 mmol) dropwise to a solution of $CH_2Cl_2$ (0.43 mL, 6.6 mmol) in THF (15 mL) with stirring at −100° C. under argon: toward the end of the BuLi addition, precipitation of the white microcrystalline $LiCHCl_2$ became evident. After 30 min, the mixture was treated with the pinanediol boronate 23b (1.368 g, 4.14 mmol) and allowed to reach 0° C. with stirring. The tetrahedral boronate adduct precipitated as a white solid at −80° C. and re-dissolved upon warming. After 1 h at 0° C., the reaction mixture was partitioned between petroleum ether (150 mL) and $H_2O$ (50 mL): the aqueous phase was extracted with petroleum ether (4×25 mL) and the combined organic phases were dried on $MgSO_4$, filtered and concentrated, giving the chloroderivative 24 as an orange oil (1.22 g, 78%), which was promptly used for the next step without further purification. (24) $^1H$ NMR ($CDCl_3$): δ 0.81 (3H, s, pinanyl $CH_3$), 1.13 (1H, d, J=10.5 Hz, pinanyl $H_{endo}$), 1.27 (3H, s, pinanyl $CH_3$), 1.38 (3H, s, pinanyl $CH_3$), 1.6-2.5 (5H, m, pinanyl protons), 3.29 (6H, s, $CH(OCH_3)_2$), 4.36 (1H, dd, J=8.8, 1.8, CHOB), 4.54 (1H, br s, ClCHB), 5.37 (1H, s, $CH(OCH_3)_2$), 7.25-7.38 (2H, m, $H_5$—$H_6$ Ph), 7.44 (1H, dt, J=6.3, 1.8 Hz, $H_4$ Ph), 7.52 (1H, s, $H_2$ Ph).

Example 21b (+)-Pinanediol (1R) 1-Acetylamino-1-(3-formylphenyl)methylboronate (25). The crude chloro-derivative 24 (434 mg, 1.15 mmol) was dissolved in THF (4 mL) and cooled to −78° C.; $LiN(TMS)_2$ (1.15 mL of a 1 M solution in THF, 1.15 mmol) was added, and the resulting solution was allowed to warm gradually to 20° C. and stirred overnight. After 16 h at rt, the reaction mixture was cooled at −78° C. and treated with a solution of $Ac_2O$ (0.435 mL, 4.6 mmol) and AcOH (79 μL, 1.38 mmol) in THF (2 mL), and then was allowed to warm to rt and stirred overnight. The solution was partitioned in EtOAc (40 mL) and $H_2O$ (10 mL), and the aqueous phase was extracted with EtOAc (30, 20, 10 mL). The combined organic phases were washed with 5% $NaHCO_3$, dried over $MgSO_4$, and concentrated in vacuo to give an orange oil which was purified by chromatography (95:5 $Et_2O$/EtOH), affording 7 (50 mg, 12% overall yield from 23b) as a pale yellow solid, mp 78-80° C., $[\alpha]_D$=−51.9 (c 0.9, $CHCl_3$), de >98%. IR (KBr): 1700, 1604 $cm^{-1}$. $^1H$ NMR ($CDCl_3$): δ 0.76 (3H, s, pinanyl $CH_3$), 1.15 (3H, s, pinanyl $CH_3$), 0.87 (1H, d, J=10.5 Hz, pinanyl $H_{endo}$), 1.24 (3H, s, pinanyl $CH_3$), 1.6-2.4 (8H, m, pinanyl protons and $CH_3CO$ at 2.18, s), 3.88 (1H, s, CHB), 4.05 (1H, dd, J=7.6 Hz, CHOB), 7.3-7.5 (2H, m, $H_5$—$H_6$ Ph), 7.61 (1H, s, $H_2$ Ph), 7.68 (1H, d, J=7.6 Hz, $H_4$ Ph), 8.8 (1H, br, NHCO), 9.96 (1H, s, CHO). $^{13}C$ NMR ($CDCl_3$): δ 25.4, 27.8, 28.6, 30.4, 37.9, 39.4, 41.3, 51.0 (br, CB), 53.8, 77.9, 67.2, 128.1, 130.2, 133.9, 137.8, 143.8, 177.4, 193.9. EIMS: m/z 355 ($M^+$), 286, 284, 259, 220, 205 (base peak), 178, 159, 149, 134, 105, 93, 83, 71, 57. Anal. Calcd for $C_{20}H_{26}BO_4$: C, 67.62; H, 7.38; N, 3.94. Found: C, 67.48; H, 7.30; N, 3.99.

Example 21c (+)-Pinanediol (1R)-1-(2-Thienylacetylamino)-1-(3-formylphenyl)methylboronate (26). The crude chloroderivative 24 (602 mg, 1.6 mmol) was dissolved in THF (4 mL) and cooled to −78° C.; $LiN(TMS)_2$ (1.6 mL of a 1 M solution in THF, 1.6 mmol) was added, and the resulting solution was allowed to warm gradually to 20° C. and stirred overnight. After 16 h at rt, the reaction mixture was cooled at −78° C., treated with a solution of 2-thiophenacetylchloride (789 μL, 6.4 mmol) and 2-thiophenacetic acid (273 mg, 1.92 mmol) in THF (4 mL), and allowed to warm to rt stirring overnight. EtOAc (90 mL) and H$_2$O (15 mL) were added, and the aqueous phase was extracted with EtOAc (50, mL). The combined organic phases were washed with 5% NaHCO$_3$, dried over MgSO$_4$, and concentrated in vacuo to give a brownish oil which was purified by gradient chromatography (100:0 to 90:10 Et$_2$O/MeOH), affording 26 (71 mg, 11% overall yield from 23b) as a pale yellow solid, mp 68-70° C., [α]$_D$=+5.0 (c 7.2, CHCl$_3$), de >98%. IR (KBr): 1698, 1601 cm$^{-1}$. $^1$H NMR (CDCl$_3$): δ 0.78 (3H, s, pinanyl CH$_3$), 0.89 (1H, d, J=10.8 Hz, pinanyl H$_{endo}$), 1.22 (3H, s, pinanyl CH$_3$), 1.30 (3H, s, pinanyl CH$_3$), 1.6-2.4 (5H, m, pinanyl protons), 3.95 (2H, s, CH$_2$CO), 4.06 (1H, s, CHB), 4.16 (1H, dd, J=8.0, 2.0 Hz, CHOB), 6.90-7.06 (2H, m, H$_4$ and H$_3$ thienyl), 7.27 (1H, m, H$_5$ thienyl), 7.32-7.50 (3H, m, H$_6$—H$_5$ Ph., NHCO), 7.59 (1H, s, H$_2$ Ph.), 7.66 (1H, m, H$_4$ Ph.), 9.91 (1H, s, CHO). $^{13}$C NMR (CDCl$_3$): δ 25.4, 27.8, 28.6, 30.1, 35.0, 37.5, 39.5, 41.2, 48.5 (br, CB), 53.5, 78.4, 85.9, 126.2, 127.6, 128.6, 128.7, 129.0, 129.6, 130.3, 133.8, 143.3, 176.5 (CONH), 193.8 (COH). EIMS: m/z 438 (M+1), 437, 297, 285, 241, 220, 205, 201, 142, 11, 97 (base peak), 93, 71, 59. Anal. Calcd for C$_{24}$H$_{23}$BNO$_5$S: C, 65.91; H, 6.45; N, 3.20; S, 7.33. Found: C, 65.80; H, 6.33; N, 3.25; S, 7.17.

We claim:

1. A method of treating a β-lactam antibiotic resistant bacterial infection comprising administering to a subject having a β-lactam antibiotic resistant bacterial infection, together with a β-lactam antibiotic, a therapeutically effective amount of a compound having a formula

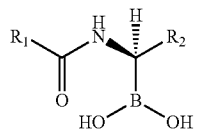

including pharmaceutically acceptable salts and solvates thereof; wherein R$_1$ is a substituent selected from hydrogen, alkyl, alkenyl, cycloalkenyl, and heterocyclyl moieties; and wherein R$_2$ is a substituent selected from heterocyclyl, cycloalkenyl, alkenyl and alkyl moieties.

2. The method of claim 1 wherein said R$_1$ substituent further comprises at least one of a hydroxy, halogen, alkoxy, amino, amido, nitro, nitrile, azo, acyl, carboxy, sulfoxy, sulfonyl, formyl, alkenyl, branched or unbranched alkyl, cycloalkyl, aminoalkyl, alkoxylalkyl, carboxylalkyl, arylalkyl, haloalkyl, azoalkyl, amidoalkyl, alkylcarbonyl, alkoxycarbonylalkyl, alkoxycarbonyl, aminocarbonyl, amidocarbonyl, arylcarboxamido, arylamino, arylcarbonyl, arylalkoxy, amidocarbonyl, carboxycarbonyl, cycloalkenyl and heterocyclyl moiety.

3. The method of claim 2 wherein said R$_1$ substituent comprises a thiophene-2-yl moiety.

4. The method of claim 1 wherein said R$_2$ substituent further comprises at least one of a carboxyl, formyl, sulfonyl, sulfoxy, heterocyclyl, cycloalkenyl, alkoxy, alkenyl, amino, amido, nitro, nitrile, azo, acyl, branched or unbranched alkyl, cycloalkyl, aminoalkyl, amidoalkyl, alkoxyalkyl and arylalkoxy moiety.

5. The method of claim 4 wherein R$_2$ comprises phenyl and one of a 3-carboxylate, a 3-formyl, a 3-sulfonate and a 3-heterocyclyl moiety.

6. The method of claim 1 wherein R$_1$ comprises a thiophene-2-yl moiety; and wherein R$_2$ comprises phenyl with a 3-carboxylate moiety.

7. The method of claim 1 wherein said β-lactam antibiotic comprises at least one of a cephalosporin, a carbapenem, a monobactam, an aminocillin and a penicillin.

* * * * *

UNITED STATES PATENT AND TRADEMARK OFFICE
CERTIFICATE OF CORRECTION

PATENT NO. : 7,928,129 B1
APPLICATION NO. : 11/901810
DATED : April 19, 2011
INVENTOR(S) : Shcoichet et al.

It is certified that error appears in the above-identified patent and that said Letters Patent is hereby corrected as shown below:

Column 1, lines 12-14:
"This invention was made with government support under Grant No. GM63815 awarded by the National Institutes of Health. The government has certain rights in the invention." should read --This invention was made with government support under Grant No. GM063815 awarded by the National Institutes of Health. The government has certain rights in the invention.--

Columns 13-14, lines 1-32:
Replace the portion of Table 1-continued as printed with the portion of Table 1-continued as originally filed below in order to correct an ommited element of the table: See Request.

Column 13, lines 54-60:
Replace the portion of Table 2 as printed with the portion of Table 2 as originally filed in order to correct a printing error within the table: See Request.

Column 14, line 36:
"refinement (A)" should read --refinement (Å)--

Column 15, line 8:
"AmpC Unexpectedly," should read --AmpC. Unexpectedly,--

Column 15, line 9:
"N62" should read --Nδ2--

Column 16, line 2:
"(K, value of 35 nM)" should read --(Ki value of 35 nM)--

Column 17, line 11:
"K, value of 1 nM," should read --Ki value of 1nM,--

Signed and Sealed this
Fifteenth Day of November, 2011

David J. Kappos
*Director of the United States Patent and Trademark Office*

CERTIFICATE OF CORRECTION (continued)
U.S. Pat. No. 7,928,129 B1

Column 17, line 16:
"AmpC Although" should read --AmpC. Although--

Column 17, line 65:
Insert a new paragraph before "Conversely,"

Column 19, line 30:
"K," should read --Ki--

Column 21, lines 35-45:
Replace the portion of Table 8 as printed with the portion of Table 8 as originally filed in order to correct a printing error within the table: See Request.

Column 21, line 56:
"Y150OH-564O$\gamma$" should read --Y150OH-S64O$\gamma$--

Column 21, line 59
"3.11" should read --3.1‡--

Column 37, line 47: "30804" should read --308 μM--

Column 38, line 4: "58804" should read --588 μM--